US010982187B2

(12) United States Patent
Funk et al.

(10) Patent No.: US 10,982,187 B2
(45) Date of Patent: Apr. 20, 2021

(54) ***BOS TAURUS* VARIETY 'HO840003150607238' AND METHODS OF USE THEREOF**

(71) Applicant: ABS Global, inc., DeForest, WI (US)

(72) Inventors: Devan Charles Funk, DeForest, WI (US); Katrina Dattilo, Waunakee, WI (US)

(73) Assignee: Genus PLC, Basingstoke (GB)

( * ) Notice: Subject to any disclaimer, the term of this patent is extended or adjusted under 35 U.S.C. 154(b) by 0 days.

(21) Appl. No.: 16/365,306

(22) Filed: Mar. 26, 2019

(65) Prior Publication Data

US 2020/0305399 A1 Oct. 1, 2020

(51) Int. Cl.
| | |
|---|---|
| *C12N 5/0735* | (2010.01) |
| *A01K 67/027* | (2006.01) |
| *C12N 5/076* | (2010.01) |
| *C12N 5/075* | (2010.01) |
| *C12N 15/877* | (2010.01) |

(52) U.S. Cl.
CPC .......... *C12N 5/0611* (2013.01); *A01K 67/027* (2013.01); *C12N 5/061* (2013.01); *C12N 5/0609* (2013.01); *C12N 15/8771* (2013.01); *A01K 2227/101* (2013.01)

(58) Field of Classification Search
CPC .... C12N 5/061; C12N 5/0611; C12N 5/0609; C12N 5/06; A01K 67/027; A01K 2227/101
See application file for complete search history.

(56) References Cited

U.S. PATENT DOCUMENTS

| | | | |
|---|---|---|---|
| 6,011,197 | A | 1/2000 | Strelchenko et al. |
| 9,868,962 | B2 | 1/2018 | May et al. |
| 2003/0157475 | A1 | 8/2003 | Schenk |

FOREIGN PATENT DOCUMENTS

| | | |
|---|---|---|
| WO | WO 2015/148761 | 10/2015 |
| WO | WO 2017/132239 | 8/2017 |

OTHER PUBLICATIONS

Printout from plant variety | InforMEA. https://www.informea.org/en/terms/plant-variety. Printed Jan. 8, 2020. pp. 3 of (Year: 2020).*
Hinch et al. Science 363, 1300 (2019) pp. 1-10 (Year: 2019).*
Bovine HapMap Consortium data set (Bovine HapMap Consortium, "Genome-wide survey of SNP variation uncovers the genetic structure of cattle breeds," Science 324(5926):528-32 (2009).
Burkard et al., "Precision engineering for PRRSV resistance in pigs: Macrophages from genome edited pigs lacking CD 163 SRCR5 domain are fully resistant to both PRRSV genotypes while maintaining biological function," PLOS Pathogens 13(2) (2017).
Cole et al., "Haplotype tests for recessive disorders that affect fertility and other traits," USDA AIP Research Report Genomic3 (Sep. 2013) updated Dec. 1, 2018, downloaded (see comment below) at aipl(dot)arsusda(dot)gov/reference/recessive_haplotypes_ARR-G3.html.
Gay et al., "Development of a Lifetime Merit-based selection index for US dairy grazing systems," J. Dairy Sci. 97:4568-4578 (2014).
Gholap et al., "Genetic Diseases in Cattle: A Review," Research Journal of Animal, Veterinary and Fishery Sciences 2(2):24-33 (2014).
Gordon et al., "Genetic transformation of mouse embryos by microinjection of purified DNA," Proc. Natl. Acad. Sci. USA 77:7380-7384 (1980).
Hammer et al., "Production of transgenic rabbits, sheep and pigs by microinjection," Nature 315: 680-683 (1985).
Illumina's Technical Note "'TOP/BOT' Strand and 'A/B' Allele", available on the internet at www(dot)illumina(dot)com/documents/products/technotes/technote_topbot.pdf (downloaded Oct. 23, 2018).
Jolly et al., "Genetic Diseases of Cattle," Chapter 21 759-777 (2010).
MacNeil et al., "Genetic relationships between feral cattle from Chirikof Island, Alaska and other breeds," Animal Genetics 38:193-197 (2007).
McClure et al., "SNP Data Quality Control in a National Beef and Dairy Cattle System and Highly Accurate SNP Based Parentage Verification and Identification," Frontiers in Genetics 9(84):1-14 (2018).
Niemann, "Transgenic pigs expressing plant genes," Proc Natl Acad Sci U S A 101:7211-7212 (2004).
Park, et al., "Role of stem cells in large animal genetic engineering in the TALENs-CRISPR era," Reprod Fertil Dev 26:65-73 (2014).
Park et al., "Genome sequencing of the extinct Eurasian wild aurochs, Bos primigenius, illuminates the phylogeography and evolution of cattle," Genome Biology 16:234 (2015).
Park et al., "Generation of germline ablated male pigs by CRISPR/Cas9 editing of the NANOS2 gene," Scientific Reports (2017).
Ross et al., "Bovine Somatic Cell Nuclear Transfer," Methods Mol Biol. 636. 155-77 (2010).
Schefers et al., "Genomic selection in dairy cattle: Integration of DNA testing into breeding programs," Animal Frontiers 2(1):1-9 (2012).
The Holstein Association USA (HAU) downloaded from www(dot)holsteinusa(dot)com/genetic_evaluations/ss_tpi_formula.htmlMar. 28, 2019.

(Continued)

Primary Examiner — Marcia S Noble
(74) Attorney, Agent, or Firm — Elizabeth A. Epstein; Michael Stimson

(57) ABSTRACT

The disclosure relates to Bovine germplasm of Bos taurus variety HO840M003150607238. Included in the present disclosure are cells comprising the genome of Bovine variety HO840M003150607238 characterized by the presence of homozygous loci and spermatozoa obtained from said cells. Also provided by the present disclosure are tissue cultures of cells, animals obtained from said cells, and parts thereof, including F1 spermatozoa. The disclosure further provides for methods of breeding, selecting, and using the germplasm to improve existing commercial cattle herds generated from in vitro fertilization methods and progeny cattle obtained from in vitro fertilization and implantation and artificial insemination methods.

22 Claims, No Drawings

Specification includes a Sequence Listing.

(56) References Cited

OTHER PUBLICATIONS

VanRaden et al., "Genetic Evaluation of Length of Productive Life Including Predicted Longevity of Live Cows," *Journal of Dairy Science* 76:2758-2764 (1993).
VanRaden et al., "Productive Life Evaluations: Calculation, Accuracy, and Economic Value," *Journal of Dairy Science* 78:631-638 (1995).
VanRaden et al., "Methods used to compute multi-trait productive life," USDA AIPL Research Report PLC (Nov. 2003) (2003).
VanRaden et al., "Net merit as a measure of lifetime profit: 2018 revision," USDA AIP Research Report NM$7 (May 2018) (2018).
Weigel et al., "Use of Linear Type and Production Data to Supplement Early Predicted Transmitting Abilities for Productive Life," *Journal of Dairy Science* 81:2040-2044 (1998).
Worley, Bovine Genome Sequencing and Analysis Consortium. "The genome sequence of taurine cattle: a window to ruminant biology and evolution," *Science* 324(5926):522-8 (2009).
Whitworth et al., "Use of the CRISPR/Cas9 System to Produce Genetically Engineered Pigs from In Vitro-Derived Oocytes and Embryos," *Biology of Reproduction* 91(3):78 (2014).
Allen A.R., et al., 2010, Compilation of a panel of informative single nucleotide polymorphisms for bovine identification in the Northern Irish cattle population. BMC Genetics 2010, 11:5.

\* cited by examiner

BOS TAURUS VARIETY 'HO840003150607238' AND METHODS OF USE THEREOF

INCORPORATION OF SEQUENCE LISTING

The Sequence Listing is hereby incorporated by reference in its entirety, including the file named P34675_ST25.txt, which is 47,645,133 bytes in size and was created on Mar. 26, 2019, which is likewise herein incorporated by reference in its entirety.

FIELD OF THE INVENTION

The present disclosure relates to the field of Bos taurus breeding. In particular, the present disclosure related to Bos taurus variety HO840003150607238 having high multi-trait selection indices and high trait transmissibility.

BACKGROUND OF THE INVENTION

There are numerous steps in the development of any new, desirable Bos taurus germplasm. Bos taurus breeding begins with the analysis and definition of problems and weaknesses of the current germplasm, the establishment of program goals, and the definition of specific breeding objectives. The next step is selection of germplasm that possess the traits to meet the program goals. A goal is to combine in a single variety an improved combination of desirable traits from the parental germplasm. See Schefers et al., "Genomic selection in dairy cattle: Integration of DNA testing into breeding programs" Animal Frontiers 2(1):1-9 (2012).

During breeding, cattle breeders have a variety of sources when making breeding decisions. In addition to genomic data, a number of agencies and organizations collect and release analysis of population data and indexes. Every three months, the Animal Improvement Programs Laboratory (AIPL) of the United States Department of Agriculture releases the newest USDA-DHIA (Dairy Herd Improvement Association) genetic evaluations for dairy bulls and cows. The AIPL calculates genetic evaluations for type for various breeds, and many breed associations provide their own indexes or other strategies for evaluating certain breed-relevant traits. U.S. dairy genetic evaluations are computed every four months by the Council on Dairy Cattle Breeding (CDCB) and Holstein Association USA (HAU). Both CDCB and HAU traits provide the breeder within important comparative data to evaluate the complex genetic and phenotypic traits to develop improved and desirable Bos taurus germplasm. For Holstein and Jersey sires, for example, evaluations are genomically enhanced and represent a blending of genomic data, pedigree information, and results from progeny. These genetic evaluations provide the breeder important information for the selection of desirable germplasm and the development of new and valuable inseminates.

There is a continuous need to develop improved Bos taurus germplasm for use in improving production herds as well as for the continued improvement of elite animals. The present germplasm is the result of crosses between superior elite females ranked by performance as among the top 1% of the population of domesticated dams and elite bulls that are among the top 5% of the domestic population.

SUMMARY OF THE INVENTION

The present disclosure comprises, in one form thereof, a plurality of Bos taurus cells each cell comprising a genome having at least 90% of the nucleic acid sequences selected from the group consisting of SEQ ID NOs:1 to 29048.

The present disclosure provides for, and includes, a plurality of Bos taurus gamete cells comprising at least 90% of the loci comprising the nucleic acid sequences selected from the group consisting of SEQ ID NOs: 1 to 29048.

In an aspect, the present disclosure includes, and provides for, an F1 Bos taurus animal, or part thereof, said F1 Bos taurus animal comprising a genome comprising at least 90% of the loci comprising the nucleic acid sequences selected from the group consisting of SEQ ID NOs: 1 to 29048.

In another aspect, the present disclosure provides for, and includes, an F1 Bos taurus animal, or part thereof, comprising a genome comprising at least 90% of the loci comprising the nucleic acid sequences selected from the group consisting of SEQ ID NOs: 1 to 29048.

In a further aspect, the present disclosure provides for, and includes a Bos taurus animal, or part thereof, comprising one or more cells having at least 25% of the loci comprising nucleic acid sequences selected from the group consisting of SEQ ID NOs:1 to 29048.

An even further aspect of the present disclosure is a plurality of Bos taurus cells, each comprising a diploid or haploid genome each diploid genome comprising homozygous loci comprising at least 90% of the nucleic acid sequences selected from the group consisting of SEQ ID NOs: 1 to 29048; and each haploid genome comprising at least 90% of the loci comprising the nucleic acid sequences selected from the group consisting of SEQ ID NOs: 1 to 29048.

DETAILED DESCRIPTION

A goal of a Bos taurus breeding program is to combine in a single Bos taurus variety an improved combination of desirable traits from the parental germplasm that provides for desirable progeny when used in artificial insemination and in vitro fertilization programs. Improved Bos taurus inseminate varieties are useful for various artificial breeding techniques, including artificial insemination ("AI") and embryo transfer ("ET"). Improved Bos taurus germplasm, varieties, and inseminates prepared therefrom, are desirable.

The present disclosure provides for, and includes, an improved elite SM germplasm obtained from a multigenerational breeding program. The germplasm is unique and readily distinguishable from germplasm present in non-selected cattle. Indeed, in the absence of continued selection, the germplasm reverts to heterogeneity and diversity. As provided herein, the germplasm of the present disclosure is identifiable using standard methods and the germplasm can be readily identified in progeny generations. Indeed, as few as 800 SNP markers are sufficient to identify parentage with greater than 99% accuracy. See McClure et al., "SNP Data Quality Control in a National Beef and Dairy Cattle System and Highly Accurate SNP Based Parentage Verification and Identification," Frontiers in Genetics 9(84):1-14 (2018). As provided here, the tens of thousands of sequences provide for tracking and selecting animals through multiple generations. Breeding with the germplasm provided herein, combined with the selection of suitable mates will maintain the desirable germplasm in subsequent generations. Moreover, genetic testing allows for the removal of progeny having germplasm that lacks that set of desired loci for the improvement of cattle herds.

The present disclosure provides for, and includes, cells, animals, and progeny of Bos taurus variety HO840003150607238 ("Animal") comprising an improved germplasm characterized by SEQ ID NOs:1 to 41648 and homozygous loci comprising the nucleic acid sequences selected from the group consisting of SEQ ID NOs:1 to 29048, and listed in Table 1. Animal differs from the reference genome at 11832 homozygous loci, or about 28% of the total loci.

TABLE 1

Genotype of *Bos taurus* animal HO840003150607238 ("Animal")

| Homozygous | SEQ ID Range SEQ ID NOs: 1 to 29048 | | No. of Alternate Alleles |
|---|---|---|---|
| | Reference Allele | Alternate Allele | |
| Chromosome 1 | 1-1110 | 17188-17963 | 775 |
| Chr. 2 | 1111-01954 | 17964-18580 | 616 |
| Chr. 3 | 1955-2883 | 18581-19199 | 618 |
| Chr. 4 | 2884-3684 | 19200-19689 | 489 |
| Chr. 5 | 3685-4439 | 19690-20169 | 479 |
| Chr. 6 | 4440-5272 | 20170-20823 | 653 |
| Chr. 7 | 5273-5962 | 20824-21347 | 523 |
| Chr. 8 | 5963-6797 | 21348-21843 | 495 |
| Chr. 9 | 6798-7455 | 21844-22309 | 465 |
| Chr. 10 | 7456-8125 | 22310-22775 | 465 |
| Chr. 11 | 8126-8809 | 22776-23290 | 514 |
| Chr. 12 | 8810-9358 | 23291-23663 | 372 |
| Chr. 13 | 9359-9951 | 23664-24058 | 394 |
| Chr. 14 | 9952-10592 | 24059-24647 | 588 |
| Chr. 15 | 10593-11148 | 24648-24987 | 339 |
| Chr. 16 | 11149-11703 | 24988-25348 | 360 |
| Chr. 17 | 11704-12314 | 25349-25729 | 380 |
| Chr. 18 | 12315-12797 | 25730-26027 | 297 |
| Chr. 19 | 12798-13309 | 26028-26360 | 332 |
| Chr. 20 | 13310-13823 | 26361-26736 | 375 |
| Chr. 21 | 13824-14279 | 26737-27082 | 345 |
| Chr. 22 | 14280-14702 | 27083-27360 | 277 |
| Chr. 23 | 14703-15016 | 27361-27615 | 254 |
| Chr. 24 | 15017-15414 | 27616-27882 | 266 |
| Chr. 25 | 15415-15770 | 27883-28107 | 224 |
| Chr. 26 | 15771-16151 | 28108-28362 | 254 |
| Chr. 27 | 16152-16444 | 28363-28574 | 211 |
| Chr. 28 | 16445-16812 | 28575-28812 | 237 |
| Chr. 29 | 16813-17187 | 28813-29048 | 235 |
| | | No. Alternate alleles | 11832 |

| Heterozygous | SEQ ID Range |
|---|---|
| Chromosome 1 | 29049-29832 |
| Chr. 2 | 29833-30576 |
| Chr. 3 | 30577-31069 |
| Chr. 4 | 31070-31789 |
| Chr. 5 | 31790-32326 |
| Chr. 6 | 32327-32899 |
| Chr. 7 | 32900-33505 |
| Chr. 8 | 33506-34086 |
| Chr. 9 | 34087-34609 |
| Chr. 10 | 34610-35231 |
| Chr. 11 | 35232-35844 |
| Chr. 12 | 35845-36305 |
| Chr. 13 | 36306-36749 |
| Chr. 14 | 36750-36970 |
| Chr. 15 | 36971-37461 |
| Chr. 16 | 37462-37865 |
| Chr. 17 | 37866-38181 |
| Chr. 18 | 38182-38494 |
| Chr. 19 | 38495-38763 |
| Chr. 20 | 38764-39143 |
| Chr. 21 | 39144-39454 |
| Chr. 22 | 39455-39787 |
| Chr. 23 | 39788-40099 |
| Chr. 24 | 40100-40457 |
| Chr. 25 | 40458-40689 |
| Chr. 26 | 40690-40949 |
| Chr. 27 | 40950-41236 |
| Chr. 28 | 41237-41401 |
| Chr. 29 | 41402-41648 |

The present disclosure provides for, and includes, a diploid Bos taurus cell or a plurality of diploid Bos taurus cells comprising improved germplasm characterized by a genome having homozygous loci comprising 90% to 100% of the nucleic acid sequences selected from the group consisting of SEQ ID NOs:1 to 29048.

Animal is the progeny of a cross between Sire HO840003135669665 ("Sire") and Dam HO840003128557405 ("Dam"). The genotype of Sire is represented by the SEQ ID NOs: 41649 to 82185 and homozygous loci comprising the nucleic acid sequences selected from the group consisting of SEQ ID NOs: 41649 to 68810 and listed in Table 2 ("Sire Genotype"). Sire differs from the reference genome at 10935 homozygous loci, or about 27% of the total loci.

TABLE 2

Genotype of Sire HO840003135669665 (Sire Genotype)

| Homozygous | SEQ ID Range SEQ ID NOs: 41649-68810 | | No. of Alternate Alleles |
|---|---|---|---|
| | Reference Allele | Alternate Allele | |
| Chromosome 1 | 41649-42719 | 57847-58601 | 754 |
| Chr. 2 | 42720-43499 | 58602-59159 | 557 |
| Chr. 3 | 43500-44453 | 59160-59783 | 623 |
| Chr. 4 | 44454-45260 | 59784-60266 | 482 |
| Chr. 5 | 45261-45934 | 60267-60700 | 433 |
| Chr. 6 | 459345-46671 | 60701-61265 | 564 |
| Chr. 7 | 46672-47422 | 61266-61885 | 619 |
| Chr. 8 | 47423-48224 | 61886-62406 | 520 |
| Chr. 9 | 48225-48890 | 62407-62852 | 445 |
| Chr. 10 | 48891-49556 | 62853-63309 | 456 |
| Chr. 11 | 49557-50233 | 63310-63817 | 507 |
| Chr. 12 | 50234-50737 | 63818-64185 | 367 |
| Chr. 13 | 50738-51301 | 64186-64534 | 348 |
| Chr. 14 | 51302-51833 | 64535-65004 | 469 |
| Chr. 15 | 51834-52378 | 65005-65353 | 348 |
| Chr. 16 | 52379-52865 | 65354-65668 | 314 |
| Chr. 17 | 52866-53404 | 65669-65967 | 298 |
| Chr. 18 | 53405-53798 | 65968-66197 | 229 |
| Chr. 19 | 53799-54206 | 66198-66464 | 266 |
| Chr. 20 | 54207-54696 | 66465-66813 | 348 |
| Chr. 21 | 54697-55109 | 66814-67072 | 258 |
| Chr. 22 | 55110-55539 | 67073-67329 | 256 |
| Chr. 23 | 55540-55826 | 67330-67565 | 235 |
| Chr. 24 | 55827-56213 | 67566-67821 | 255 |
| Chr. 25 | 56214-56566 | 67822-68028 | 206 |
| Chr. 26 | 56567-56940 | 68029-68274 | 245 |
| Chr. 27 | 56941-57230 | 68275-68477 | 202 |
| Chr. 28 | 57231-57518 | 68478-68648 | 170 |
| Chr. 29 | 57519-57846 | 68649-68810 | 161 |
| | | No. Alternate alleles | 10935 |

| | SEQ ID Range |
|---|---|
| Heterozygous | 68811-82185 |
| Chromosome 1 | 68811-69568 |
| Chr. 2 | 69569-70363 |
| Chr. 3 | 70364-70760 |
| Chr. 4 | 70761-71423 |
| Chr. 5 | 71424-72041 |
| Chr. 6 | 72042-72719 |
| Chr. 7 | 72720-73111 |
| Chr. 8 | 73112-73656 |
| Chr. 9 | 73657-74158 |
| Chr. 10 | 74159-74759 |
| Chr. 11 | 74760-75333 |
| Chr. 12 | 75334-75787 |
| Chr. 13 | 75788-76276 |
| Chr. 14 | 76277-76695 |
| Chr. 15 | 76696-77157 |
| Chr. 16 | 77158-77633 |
| Chr. 17 | 77634-78084 |
| Chr. 18 | 78085-78534 |

TABLE 2-continued

Genotype of Sire HO840003135669665 (Sire Genotype)

| | |
|---|---|
| Chr. 19 | 78535-78953 |
| Chr. 20 | 78954-79354 |
| Chr. 21 | 79355-79764 |
| Chr. 22 | 79765-80082 |
| Chr. 23 | 80083-80419 |
| Chr. 24 | 80420-80769 |
| Chr. 25 | 80770-81008 |
| Chr. 26 | 81009-81269 |
| Chr. 27 | 81270-81548 |
| Chr. 28 | 81549-81839 |
| Chr. 29 | 81840-82185 |

The genotype of Dam is represented by the SEQ ID NOs: 82186-122589 and homozygous loci comprising the nucleic acid sequences selected from the group consisting of SEQ ID NOs: 82186 to 98686 and listed in Table 3 ("Dam Genotype"). Dam differs from the reference genome at 11237 homozygous loci, or about 28% of the total loci.

TABLE 3

Genotype of Dam HO840003128557405 ("Dam Genotype")

| | SEQ ID Range SEQ ID NOs: 82186-98686 | | No. of Alternate |
|---|---|---|---|
| Homozygous | Reference Allele | Alternate Allele | Alleles |
| Chromosome 1 | 82186-83192 | 98687-99371 | 754 |
| Chr. 2 | 83193-84062 | 99372-99977 | 557 |
| Chr. 3 | 84063-84881 | 99978-100492 | 623 |
| Chr. 4 | 84882-85725 | 100493-101051 | 482 |
| Chr. 5 | 85726-86405 | 101052-101490 | 433 |
| Chr. 6 | 86406-87219 | 101491-102080 | 564 |
| Chr. 7 | 87220-87869 | 102081-102587 | 619 |
| Chr. 8 | 87870-88653 | 102588-103065 | 520 |
| Chr. 9 | 88654-89284 | 103066-103516 | 445 |
| Chr. 10 | 89285-89899 | 103517-103940 | 456 |
| Chr. 11 | 89900-90666 | 103941-104564 | 507 |
| Chr. 12 | 90667-91210 | 104565-104932 | 367 |
| Chr. 13 | 91211-91734 | 104933-105256 | 348 |
| Chr. 14 | 91735-92282 | 105257-105760 | 469 |
| Chr. 15 | 92283-92836 | 105761-106060 | 348 |
| Chr. 16 | 92837-93376 | 106061-106423 | 314 |
| Chr. 17 | 93377-93940 | 106424-106775 | 298 |
| Chr. 18 | 93941-94380 | 106776-107030 | 229 |
| Chr. 19 | 94381-94873 | 107031-107351 | 266 |
| Chr. 20 | 94874-95367 | 107352-107726 | 348 |
| Chr. 21 | 95368-95770 | 107727-108041 | 258 |
| Chr. 22 | 95771-96219 | 108042-108305 | 256 |
| Chr. 23 | 96220-96562 | 108306-108588 | 235 |
| Chr. 24 | 96563-96993 | 108589-108894 | 255 |
| Chr. 25 | 96994-97303 | 108895-109070 | 206 |
| Chr. 26 | 97304-97640 | 109071-109263 | 245 |
| Chr. 27 | 97641-97962 | 109264-109489 | 202 |
| Chr. 28 | 97963-98283 | 109490-109703 | 170 |
| Chr. 29 | 98284-98686 | 109704-109952 | 161 |
| | | No. Alternate alleles | 11237 |

| | SEQ ID Range |
|---|---|
| Heterozygous Chromosome 1 | 109953-122589 109953-110857 |
| Chr. 2 | 110858-111511 |
| Chr. 3 | 111512-112144 |
| Chr. 4 | 112145-112680 |
| Chr. 5 | 112681-113278 |
| Chr. 6 | 113279-113859 |
| Chr. 7 | 113860-114455 |
| Chr. 8 | 114456-115061 |
| Chr. 9 | 115062-115588 |
| Chr. 10 | 115589-116273 |
| Chr. 11 | 116274-116642 |
| Chr. 12 | 116643-117065 |

TABLE 3-continued

Genotype of Dam HO840003128557405 ("Dam Genotype")

| | |
|---|---|
| Chr. 13 | 117066-117610 |
| Chr. 14 | 117611-117973 |
| Chr. 15 | 117974-118467 |
| Chr. 16 | 118468-118832 |
| Chr. 17 | 118833-119198 |
| Chr. 18 | 119199-119559 |
| Chr. 19 | 119560-119828 |
| Chr. 20 | 119829-120190 |
| Chr. 21 | 120191-120554 |
| Chr. 22 | 120555-120841 |
| Chr. 23 | 120842-121068 |
| Chr. 24 | 121069-121323 |
| Chr. 25 | 121324-121625 |
| Chr. 26 | 121626-121970 |
| Chr. 27 | 121971-122194 |
| Chr. 28 | 122195-122406 |
| Chr. 29 | 122407-122589 |

Notably, and as expected for a select cross between Sire and Dam, the number of homozygous alleles in Animal increases compared to both parents. As show in Table 4, Animal retains 70 to 80% of the homozygous alleles found in Sire and Dam and more than 15% of the heterozygous alleles in Sire and Dam are fixed as homozygous in Animal. These results demonstrate that improvements by selective are breeding are reflected in the germplasm and that such improvements do not require, but may be informed by, a priori knowledge of the genotype of the germplasm.

TABLE 4

Select cross increases homozygosity

| Alleles | Sire | Dam | Admiral | Homozygous Matches from parent | | Just Parent type | |
|---|---|---|---|---|---|---|---|
| | | | | S % | D % | S % | D % |
| Homo ref | 12944 | 13040 | 17187 | 32% | 32% | 80% | 79% |
| Homo alt | 8663 | 8313 | 11832 | 21% | 21% | 79% | 74% |
| Homo-homo | 21607 | 21353 | 29048 | 54% | 53% | 80% | 77% |
| Het to homo | 6724 | 6340 | | 17% | 16% | 50% | 50% |

It is to be understood that the disclosure is not necessarily limited in its application to the details set forth in the following description or exemplified by the Examples. The disclosure is capable of other aspects or of being practiced or carried out in various ways.

As used herein the term "about" refers to ±10%.

As used herein, the singular forms "a," "an," and "the" include plural references unless the context clearly dictates otherwise. For example, the term "a compound" or "at least one compound" may include a plurality of compounds, including mixtures thereof Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3," "from 1 to 4," "from 1 to 5," "from 2 to 4," "from 2 to 6," "from 3 to 6," etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

For the purposes of this invention the term "semen" means seminal fluid which may contain sperm (also referred to as "spermatozoa") secreted by the gonads of a male animal which can be collected from the male animal by a variety of methods such as use of an artificial vagina, manual manipulation of the penis, electrical manipulation of the anus, or the like.

As used herein, "locus", or plural "loci", refers to a physical site or location of a specific gene or marker on a chromosome. Loci of the present disclosure include, and are identifiable by, a SEQ ID NO, each SEQ ID NO providing the identity of the polymorphism at a single nucleotide polymorphic site and the adjacent 100 base pairs.

Loci may also characterized as either 'A' loci, 'B' loci, or heterozygous 'A/B' loci. The identification of loci as either 'A' or 'B' loci is determined according to the top (TOP) and bottom (BOT) designations based on the polymorphism itself, or the contextual surrounding sequence as developed by Illumina. Methods for determining the designation of a polymorphic site as 'A' or 'B' are known in the art, for example as provided by Illumina's Technical Note entitled "'TOP/BOT' Strand and 'A/B' Allele", available on the internet at www(dot)illumina(dot)com/documents/products/technotes/technote_topbot.pdf. The NCBI's dbSNP database has adopted the TOP/BOT nomenclature in 2005 and the designation is well known to those of skill in the art. As shown in the Examples, through sequence comparison extensive information about each loci is available to a person of ordinary skill in the art, including, but not limited to, dbSNP identifier, sources, chromosomal location, genes, transcripts, linkage to genes or quantitative trait loci (QTL), and interactions.

As used herein, "germplasm" means an intact genome present in cells or nuclei and comprising chromosomes. In diploid cells, the germplasm is characterized by the presence of sequences representing the sequences at polymorphic sites (e.g., SNPs) that are homozygous or heterozygous. As used herein, the germplasm of the present disclosure is characterized by the homozygous loci. In haploid cells (e.g., ova or sperm), the each of the sequences at each homozygous loci in the parent are present in each cell. In contrast, heterozygous loci are present in haploid germplasm according to random assortment. Accordingly, the genotype at heterozygous loci in haploid cells varies from haploid cell to haploid cell, while the sequences of the homozygous loci from the parent are present in each haploid cell and are therefore faithfully transmitted to progeny.

During breeding, to maintain and improve the germplasm, selections of a second parent may be an elite second parent having superior traits. As demonstrated in the examples, such select crosses result in progeny that retain significant numbers of homozygous loci present in each elite parent and further result in additional loci becoming homozygous. Thus, select crosses result in some or all of the homozygous loci of the Bos taurus cells of the present disclosure being retained in progeny generations. Generally, locus homozygosity is maintained when the second parent is an elite parent with high trait values as described below. Similarly, the improved germplasm of the present disclosure can be maintained by selecting superior breeding partners in the F1 and later progeny generations. By suitable selection of the second parent, the germplasm can be maintained at the homozygous loci. Even further, careful selection of elite breeding partners results increased numbers of homozygous loci as the preferred allele at the heterozygous loci are homozygosed in elite progeny. Notably, knowledge of the underlying biology is helpful, but not required.

As used herein, "gamete" refers to a haploid germ cell and includes either a sperm or an ovum and may be used interchangeably. Generally, the identity as a sperm or an ovum can be determined by the context as bulls produced sperm and dams produce ova. For the purposes of this invention the term "sperm" means the haploid cell that is the gamete of a male animal which may join an egg (also referred to as "ovum") to produce a zygote and broadly encompasses infertile sperm, sperm having a comparably lesser or a comparably greater fertility between a first amount of sperm obtained from a first animal and a second amount of sperm obtained from a second animal and which may be obtained in the form of a raw ejaculated semen, frozen semen, as sperm separated from the semen and contained in an extender or diluent, or as sex-selected sperm.

As used herein, the term "inseminate" is intended to broadly encompass an amount of sperm whether contained in semen together with a cryoprotectant. Inseminates may optionally include one or more "extenders" and diluents which can be utilized to fertilize the eggs of a female animal whether in vitro or in vivo. As used herein, inseminates can further include sex-selected sperm compositions.

As used herein, the term "sex-selected sperm" means sperm which have been separated, regardless as to the method of separation, into subpopulations containing X-chromosome bearing sperm and Y-chromosome bearing sperm having a purity in the range of about 70 percent ("%") and about 100%.

Predicted Transmitting Abilities (PTAs) can be computed for various traits, for example in the broad categories of production (milk and milk components), health/fitness, and type. Dairy cattle are evaluated for the traits of milk, fat, and protein yield, length of productive life, and somatic cell score (an indicator of mastitis). Evaluation procedures combine information from relatives of an evaluated animal, and from the animal itself in the case of cows. Additionally, numerous type or conformation traits are evaluated routinely.

An important aspect of Bos taurus breeding programs are genetic values for yield, management traits, and type that are reported as PTAs. These important traits include higher milk, protein and fat yield PTAs shown as added pounds of milk, fat, and protein expected per lactation for average daughters of individual sires. PTAs are also expressed as percentage traits that are represented as percentage point differences where plus values indicate higher concentration of fat and protein in milk. Bos taurus animals and cells obtained therefrom are also selected to provide increased numbers of daughters and herds contributing to production, improved reliability, improved productive life, improved somatic cell score (SCS). Desirable Bos taurus varieties provide higher daughter pregnancy rates (DPR) that are a genetic measure of the percentage of non-pregnant cows that become pregnant during each 21-day period (heat cycle). Another important and desirable PTA selected by breeders is the productive life (PL) that is the additional months of life in the milking string. Also included among the desirable PTAs are calving related traits such as the service sire calving ease and the service sire stillbirth.

Traits are typically combined into an index based on their relative economic weights. For example, the Net Merit index (NM$) computed by USDA AWL estimates lifetime profit based on incomes and expenses relevant for today's dairy producers and is expressed as a dollar value. Traits included in NM$ are: protein (lb.), fat (lb.), productive life, somatic cell score, udder composite, feet/legs composite, body size composite and daughter pregnancy rate. Calving ability also is included in NM$ calculations for Holsteins and Brown Swiss. The traits incorporated into calving ability for Holsteins are daughter stillbirth, service sire stillbirth, daughter calving ease, and service sire calving ease. Only the two calving ease traits are available for inclusion in calving ability values of Brown Swiss. Net merit scores are a relative score calculated based on a comparison with a baseline average animal in 2010. A new baseline animal based on the average animal in 2015 is expected to begin use in 2020 and will reflect improvements to dairy herds generally. Under the new NM$, it is anticipated that NM$ scores in 2020 will be reduced by about 150 to 200 points compared to earlier NM$ scores. As used herein, NM$ scores are calculated using the 2010 baseline and persons of ordinary skill in the art will be to calculate or convert NM$ values based on the 2010 baseline population and 2015 baseline population.

Holstein Association USA calculates the Total Performance Index (TPI). It includes the traits of protein, fat, type, udder composite, feet and leg composite, daughter pregnancy rate, productive life, somatic cell score, daughter calving ease, daughter stillbirth and dairy form. Like Net merit scores, TPI is calculated based on a comparison with a baseline average animal in 2010, however, the Holstein Association USA has not announced plans to update the baseline animal. Accordingly, as used herein, TPI scores are calculated using a 2010 baseline animal. However, should a new baseline year be adopted, persons of ordinary skill in the art will be able to calculate or convert TPI values based on the 2010 baseline population any future baseline animal.

The Jersey Performance Index (JPI), which is used by the American Jersey Cattle Association, is comprised of the following traits: protein, fat, functional trait index, productive life, somatic cell score, and daughter pregnancy rate. Functional trait index is based on the bull/cow PTAs for all type traits.

Using a selection index can be an effective way to consider several traits when choosing breeding stock. Conventional animal husbandry strategies often rely on selection indexes, particularly for choosing service sires.

Breeding stock sires and sire lines are typically chosen based upon their size and fertility. Prior successes in mating as well as siring females are both traits that are often utilized in selecting sires and/or sire lines.

Also, knowing where service sires rank relative to other active bulls is typically considered to be helpful in determining if the sires meet a particular herd's genetic goals. Selection indexes can be particularly useful in monitoring such ranking. To maximize genetic improvement using a selection index, it is usually recommended that the service sires for a given herd average at or above the 80th percentile.

In germplasm improvement programs, "Dams of Males" (DM) or more commonly, "bull mothers" represent a group of elite females that are selected based on EBV or GEBV and that usually rank among the top 1% of the population. These cows are typically mated to elite bulls from the "Sires of Males" (SM) group for the purpose of producing bull calves.

"Sires of males" (SM) or "sires of sons" are elite males that are also selected by EBV or GEBV to be sires of the next generation of young bulls and represent <5% of the males. It is the SM semen that is marketed to dairy farmers and it is primarily through the distribution of SM semen that commercial herds are improved.

Sires of females (SF) or "active AI sires" represent a larger group of males that have been selected based on EBV or GEBV and whose semen is used to breed the general population and produce replacement females for commercial farms.

"Dams of Females" (DF) or "commercial cows" represent the large population of females that are primarily used to produce milk rather than breeding stock and are routinely mated to bulls from the "Sires of Females" (SF) group to initiate lactation, resulting in the next generation of replacement heifers.

Germplasm development programs are directed to the continued improvement of the elite (DM and SM) individuals that in turn improve the germplasm of the larger DF and SF populations. Distinct DM and SM lines have been developed to serve different markets and the resulting germplasms are distinct. That is, different DM and SM lines have distinctive sets of alleles as a result of multigenerational selections.

Ranchers and dairy farmers increase the value of a cow's calves by utilizing frozen semen from the most valuable SM bulls in the industry to breed their cows. Frozen semen can be shipped commercially around the world, the best bulls can be mated to thousands of cows instead of the usual 20 to 40 under natural pasture mating conditions. Once thawed, the semen can be used as an inseminate.

As used herein, daughter pregnancy rate (DPR) is a genetic measure of the percentage of non-pregnant course that become pregnant during each 21-day period (heat cycle). DPR is similar, but not exactly the same, as pregnancy rates computed for herd management purposes. Daughters or sires which have larger PTA DPR are more likely to conceive during a given heat cycle and each 1% increase in PTA DPR is associated with a genetic decrease of 4 days open.

As used herein, Cow Livability (LIV) represents the additional percentage of cows that avoid dying on the farm, permitting producers to recoup disposal income. The trait similar to PL which includes cows culled from the herd for any reason. LIV values range from about −5 to +5, where 5% more of a bull's daughters will remain alive compared to the breed average.

As used herein, heifer conception rate (HCR) is the percentage of inseminated heifers that become pregnant at each service; shown as a deviation in percentage.

As used herein, cow conception rate (CCR) is the percentage of inseminated cows that become pregnant at each service; shown as a deviation in percentage.

As used herein, estimated future inbreeding (EFI) is the estimate of future progeny inbreeding, assuming that an animal is mated randomly within their given breed.

As used herein, kappa casein (K-casein) identify sires with homozygous BB genotype for Kappa Casein for preferred cheese production.

As used herein, predicted transmitting ability protein (PTAP) is a yield trait for protein measured in pounds that is the predicted difference of the protein yield of the offspring from the average. PTAP is shown as added pound of protein expected per lactation for average daughters of individual sires. Higher numbers are preferred.

As used herein, predicted transmitting ability fat (PTAF) is a yield trait for fat measured in pounds that is the predicted difference of the fat yield of the offspring from the average. PTAF is shown as added[or added?] pound of fat expected per lactation for average daughters of individual sires. Higher numbers are preferred.

As used herein, predicted transmitting ability milk (MILK or PTA MILK) is a yield trait for milk measured in pounds that is the predicted difference of the milk yield of the offspring from the average. MILK is shown as added pounds of milk expected per lactation for average daughters of individual sires. Higher numbers are preferred.

As used herein, feed efficiency value (FE) recognizes cattle with the ability to produce large volumes of milk without having to consume a great deal of feed, based on the following formula: Feed Efficiency=(Dollar value of milk produced)−(Feed costs for extra milk)−(Extra maintenance costs).

As used herein, predicted transmitting ability type (PTAT or TYPE) is represented as differences in points from a base population. Daughter final scores are collected by breed classifiers. Raw scores then are adjusted for cow age and used to derive Type PTAs (PTAT). These PTAT are represented as differences in points from the base population. TYPE values are normalized to enable comparisons across different base populations through time.

As used herein, STA dairy form (DF or DFM), formerly known as "dairy character", refers to sharpness, angularity, flatness of bone, openness of rib and length of neck that provides an indication of 'milkiness' and reflects the ability of a dairy cow to produce milk from the feed over flesh and fat.

Dairy cattle are evaluated and described using a criteria generally known as linear descriptive traits that are well known in the art. These linear descriptive traits include Stature (STA), Strength (STR), Body Depth (BDE), Rump Angle (RPA), Thurl Position, Rump Width, Fore Udder Height (FTA), Fore Udder Attachment (FUA), Rear Udder Height (RUH), Rear Udder Width (RUW), Udder Cleft (UCL), Udder Depth (UDP), Front Teat Placement (FTP), Rear Teat Placement (RTP), Teat Length (TLG), Udder Tilt (?), Rear Legs (Side View) (RLS), Rear Legs, (Rear View) (RLR), Feet Leg Score (FLS), Foot Angle, and Body Condition. These linear trait criteria are well known to those skilled in the art. See for example, The Diary Cow Today: U.S. Trends, Breeding, and Progress Since 1980, S. L. Spahr and G. W. Opperman, Chapter 9, Type and classification and trait appraisal, hereby incorporated by reference in its entirety.

Linear descriptive traits are often combined into composite indexes to simplify the process of describing the transmitting pattern for type traits. Composite indexes include the feet & legs composite (FLC), the udder composite index (UDC), the body form (BF) composite index, body size composite (BSC) index, and the dairy capacity (DC) composite index. The FLC composite is a combination of rear legs, side view and foot angle linear traits. The UDC incorporates the udder attachment, rear udder height, rear udder width, udder depth, udder cleft, front teat placement, and rear teat placement linear traits. The UDC is designed so that the association between UDC and herd life is maximized. Larger values are associated with longer herd life. The BF index combines the linear traits of stature, body depth, rump angle, and rump width. The DC composite combines the linear traits of dairy form and strength. The BSC is another composite index calculated from four linear traits: stature, strength, body depth and rump width. Every 1.0 STA increase in the BSC correlates with a 24 pound predicted increase in mature body weight.

As used herein, "Productive Life" (PL) is a measure of how long dairy cows survive in a herd after they calve for the first time. It is based on calving dates, culling or death dates, and days in milk (based on dry dates) in each lactation for cows on DHI test. The PTA for Productive Life (PL) is expressed as additional months of life in the milking string. Bulls with larger PTA PL are expected to sire daughters that have longer productive lives. Data used to compute PTA PL include actual longevity, stage of lactation, and culling data supplemented with data from traits that are correlated with PL. By assigning the largest PL credits for months in peak production and by giving later lactations slightly more credit than first lactation, PL reflects the economic impact of cow longevity. The heritability of PL is low at 0.085 and the trait is expressed late in the life of dairy cow. Accordingly, PL is a difficult trait to improve through selection because of low heritability and expression of the trait late in life. Methods for calculating PL are known in the art. See VanRaden et al., "Genetic Evaluation of Length of Productive Life Including Predicted Longevity of Live Cows," *Journal of Dairy Science* 76:2758-2764 (1993), VanRaden et al., Productive Life Evaluations: Calculation, Accuracy, and Economic Value *Journal of Dairy Science* 78:631-638 (1995), Weigel et al., "Use of Linear Type and Production Data to Supplement Early Predicted Transmitting Abilities for Productive Life," *Journal of Dairy Science* 81:2040-2044(1998), see also VanRaden et al., "Methods used to compute multi-trait productive life," USDA AIPL Research Report PLC (11-03) available at aipl(dot)arsusda(dot)gov/reference/multi-pl.htm. Each of the foregoing references are hereby incorporated by reference in their entireties. The present disclosure provides for, and includes, progeny cattle having an increased PL relative to a dam parent.

As used herein, "Somatic Cell Score" (SCS) is calculated from the Somatic Cell Count (SCC). When milk is produced, a small number of cells, are also transferred to the milk (along with the proteins, fat, water, and minerals that make up milk). Although all milk contains some of these cells, milk quality is affected if they are present in very high numbers. Milk processors limit the amount they will allow in milk they buy from farmers. Also, knowing the SCS for an individual cow can help the farmer tell if the cow is healthy because irritation in the udder can cause higher SCS. Health management has the biggest effect on SCS, but just like some people inherit a higher chance of getting ear infections, cows can inherit traits which cause higher SCS. Next to traits like milk or protein production, SCS has a low heritability. Somatic Cell Score PTA is calculated using somatic cell score data from the first five lactations as an indicator of mastitis resistance. Bulls with lowest PTA SCS are expected to sire daughters with lowest SCS, lowest somatic cell counts (SCC), and the fewest cases of mastitis. The present disclosure provides for, and includes, reduced SCS in progeny compared to a dam parent.

As used herein, "Fertility Index" (FI) combines several reproductive components into one overall index: ability to conceive as a maiden heifer, ability to conceive as a lactating cow, and a cow's overall ability to start cycling again, show heat, conceive, and maintain a pregnancy. The Fertility Index is derived from the formula: Fertility Index=18% Heifer Conception Rate (HCR)+18% Cow Conception Rate (CCR)+64% Daughter Pregnancy Rate (DPR). The present disclosure provides for, and includes, an increased FI in progeny compared to a dam parent. Also included are methods to improve FI in an offspring comprising crossing an Animal of the present disclosure with dams of a herd in need of improvement.

As used herein, "Sire Calving Ease" (SCE) measures the tendency of calves from a particular sire to be born more or less easily and is express as a percent of difficult births in first calf heifers on a scale of 1 to 5 (1 is classified as "no problem"). The percent difficult birth among Holstein is about 8%. Generally, bulls having an SEC of 8% or less are considered "calving ease" bulls. Lower numbers are preferred. The present disclosure provides for, and includes, reduced SCE of progeny cattle. Also included are methods to improve SCE in a progeny comprising crossing an Animal of the present disclosure with dams of a herd in need of improvement.

As used herein, "Daughter Calving Ease" (DCE), like SCE, is a measurement of the tendency of calve from a particular animal to be born more or less easily. Lower numbers are preferred. The present disclosure provides for, and includes, reduced DCE of progeny cattle. Also included are methods to improve DCE in a progeny comprising crossing an Animal of the present disclosure with dams of a herd in need of improvement.

As used herein, "Service Sire Stillbirth" (SSB) expresses the proportion of stillborn calves expected from sires. The genetic base for Stillbirth is 8%. The present disclosure provides for, and includes, reduced SSB of progeny cattle relative to the genetic base. In an aspect, the progeny cattle have an SSB below 5%. Also included are methods to improve SSB in a progeny comprising crossing an Animal of the present disclosure with dams of a herd in need of improvement.

As used herein, "Daughter Stillbirth" (DSB) is the tendency of calves from a sire to be stillborn and applies to the Holstein breed only. As discussed below, DSB can be related to certain haplotypes. The present disclosure provides for, and includes, reduced DSB of progeny cattle relative to the genetic base. In an aspect, the progeny cattle have a DSB below 5%. Also included are methods to improve DSB in a progeny comprising crossing an Animal of the present disclosure with dams of a herd in need of improvement.

As used herein, TPI® is a multi-trait selection index published by the Holstein Association USA (HAU) and is calculated using methods known in the art (Available on the internet at www(dot)holsteinusa(dot)com/genetic_evaluations/ss_tpi_formula.html. TPI® incorporates production, management, Type, and important linear and composite traits. TPI® focuses on dairies paid for protein plus fat and requiring more emphasis on Type.

Breeders have developed merit measures for the evaluation of value of improved Bos taurus germplasm over the lifetime of offspring. Various merit measures account for the additional net profit that an offspring of an animal will provide over its lifetime. Income and expenses for a typical dairy operation have been estimated, so that a measure of overall net profit can be calculated. Three different values (Net, Fluid and Cheese) of lifetime profitability are available. The primary difference between the formulas is the emphasis that is placed on the components. When breeding, producers select the index that is closest to the milk payment in their area. Net merit is based upon the future anticipated average milk price for all of the U.S. Fluid Merit would be for producers who do not receive any payment for protein. In the Fluid Merit formula a negative value is placed on protein because additional feed is required to produce additional protein. Without a direct payment for the additional protein, this results in a negative value. Cheese Merit may be appropriate for farmers selling their milk directly to a cheese plant.

As used herein, lifetime net merit (NM$) is a multi-trait selection index published by CDCB. Methods to calculate NM$ are known in the art. See VanRaden et al., "Net merit as a measure of lifetime profit: 2018 revision," USDA AIP Research Report NM$7 (5-18) (2018) available at aipl(dot)arsusda(dot)gov/reference/nmcalc-2018.htm, hereby incorporated by reference in its entirety. The NM$ incorporates production, management and important composite traits and is designed for dairies paid for protein plus fat and requiring more emphasis on management traits. The present disclosure provides for, and includes, increased NM$ of progeny cattle relative to parents. In an aspect, the NM$ of progeny cattle is increased by at least 10% over the parent generation. Also included are methods to improve NM$ in a herd comprising crossing an Animal of the present disclosure with dams of a herd in need of improvement.

Trait parameters have been correlated with the underlying genetics and the heritabilities determined. The genetic and phenotypic correlations among the twelve PTA traits are also provided by VanRaden et al., 2018.

As used herein, grazing merit (GM$) is an index that incorporates economic values appropriate for grazing production in the U.S. The GM$ index is based upon appropriate costs and revenues to allow for selection of cows and bulls for more optimal genetic progress. GM$ is geared toward herds on pasture systems, with those breeders often demanding higher fertility, compared to conventional systems, due to seasonal calving requirements. Methods to calculate GM$ are known in the art. See Gay et al., "Development of a Lifetime Merit-based selection index for US dairy grazing systems," J. Dairy Sci. 97:4568-4578 (2014), hereby incorporated by reference in its entirety. The present disclosure provides for, and includes, increased GM$ of progeny cattle relative to parents. In an aspect, the GM$ of progeny cattle is increased by at least 10% over the parent generation. Also included are methods to improve GM$ in a herd comprising crossing an Animal of the present disclosure with dams of a herd in need of improvement.

As used herein cheese merit (CM$) is an index that incorporates economic values appropriate for the production of cheese. The present disclosure provides for, and includes, increased CM$ of progeny cattle relative to parents. In an aspect, the CM$ of progeny cattle is increased by at least 10% over the parent generation. Also included are methods to improve CM$ in a herd comprising crossing an Animal of the present disclosure with dams of a herd in need of improvement.

As used herein, fluid merit (FM$) is an index that incorporates economic values for dairy production wherein the producers do not receive any payment for protein. Methods for calculating FM$ are known in the art. The present disclosure provides for, and includes, increased FM$ of progeny cattle relative to parents. In an aspect, the FM$ of progeny cattle is increased by at least 10% over the parent generation. Also included are methods to improve FM$ in a herd comprising crossing an Animal of the present disclosure with dams of a herd in need of improvement.

As used herein, a haplotype is a combination of alleles (DNA sequences) at different locations on a chromosome that are transmitted together as a group (linked). Haplotype tests are available that provide for the identification of recessive disorders that affect fertility and other traits. See Cole et al., "Haplotype tests for recessive disorders that affect fertility and other traits," USDA AIP Research Report Genomic3 (09-13) updated Dec. 1, 2018, available at aipl (dot)arsusda(dot)gov/reference/recessive_haplotypes_ARR-G3.html, hereby incorporated by reference in its entirety. As shown in Table 5, certain haplotypes are undesirable in a Bos taurus germplasm as provided in the present specification. When the recessive haplotype is homozygous, fertility and other critical traits are significantly affected. The germplasm of the present disclosure can be used to improve herds and reduce the presence of these undesirable haplotypes.

TABLE 5

Haplotypes impacting fertility

| Breed | Haplotype | OMIA* 9913 ID | Functional/ gene name | Frequency (%) | Chromosome |
|---|---|---|---|---|---|
| Holstein | HBR | 001199 | Black/red coat color/ MC1R(MSHR) | 0.8 | 18 |
| | HDR | 001529 | Dominant red coat color | 0.04 | 3 |
| | HH0 | 000151 | Brachyspina/FANCI | 2.76 | 21 |
| | HH1 | 000001 | APAF1 | 1.92 | 5 |
| | HH2 | 001823 | — | 1.66 | 1 |
| | HH3 | 001824 | SMC2 | 2.95 | 8 |
| | HH4 | 001826 | GART | 0.37 | 1 |
| | HH5 | 001941 | — | 2.22 | 9 |
| | HHB | 000595 | BLAD/ITGB2 | 0.25 | 1 |
| | HHC | 001340 | CVM/SLC35A3 | 1.37 | 3 |
| | HHD | 000262 | DUMPS/UMPS | 0.01 | 1 |
| | HHM | 000963 | Mulefoot/LRP4 | 0.07 | 15 |
| | HHP | 000483 | Polledness/POLLED | 0.71 | 1 |
| | HHR | 001199 | Red coat color/ MC1R(MSHR) | 5.42 | 18 |
| Jersey | JH1 | 001697 | CWC15 | 12.10 | 15 |
| | JH2 | 001942 | — | 1.3 | 26 |
| | JHP | 000483> | Polledness/POLLED | 2.2 | 1 |

In aspects according to the present disclosure, the Bos taurus germplasm is free of certain haplotypes that negatively impact fertility. Five haplotypes impacting fertility of Holstein breeds, referred to as HH1, HH2, HH3, HH4 and HH5, are believed to cause embryonic or fetal death when present in homozygous form, i.e., the offspring inherits the haplotype from both the sire and dam. In a herd, this would appear as if a cow did not conceive, resulting in greater days open and lower conception rates. Researchers have found that these haplotypes never occur in homozygous form amongst any living animal (that had their genome tested; the group researchers studied). That scenario is highly unlikely based on population probabilities, unless affected animals did not survive to birth.

Cattle suffer from a number of genetic diseases that are monogenic disorders inherited in a Mendelian fashion. A number of these genetic diseases are presented below together with their genetic codes. Various genetic diseases are known in the art. See for example, Garrick and Ruvinsky, "The Genetics of Cattle," $2^{nd}$ Edition, CAB International, Oxfordshire UK 2015; see also Parkinson et al., "Diseases of Cattle in Australasia," ISBN 9780958363447 Jolly et al., "Genetic Diseases of Cattle," Chapter 21; and vetbook(dot) org/wiki/cow/index.php/Genetic_diseases_of_cows, hereby incorporated by reference in their entireties. The germplasm of the present disclosure can be used to reduce the presence of these recessive genes in herds and bovine populations.

TABLE 6

Genetic Codes of Recessive Genes

| Genetic Code | Phenotype | Genetic Code | Phenotype |
|---|---|---|---|
| BD | Bulldog* | ACAN | Dwarfism |
| BL | Bovine Leukocyte Adhesion Deficiency (BLAD)* | PO | Observed Polled** |
| TL | Tested free of BLAD | PC | Tested Heterozygous Polled** |
| BY | Brachyspina* | PP | Tested Homozygous Polled** |
| TY | Tested free of Brachyspina | TP | Tested free of the Polled Condition (horned) |
| CV | Complex Vertebral Malformation (CVM)* | PT | Pink Tooth (Porphyria)* |
| TV | Tested free of CVM | RC | Carrier for red hair color* |
| DP | Deficiency of Uridine Monophosphate Synthase (DUMPS)* | B/R | Black/Red hair color* |
| TD | Tested free of DUMPS | TR | Tested free to red hair color |
| MF | Mulefoot* | DR1 | Tested Heterozygous for Dominant Red* |
| TM | Tested free of Mulefoot | DR2 | Tested Homozygous for Dominant Red** |

*Recessive gene carrier
**Dominant gene carrier

The present disclosure provides for and includes Bos taurus germplasm that is free of carriers of recessive genes selected from the group consisting of Bulldog (BD), Bovine Leukocyte Adhesion Deficiency (BL), brachyspina (BY), Complex Vertebral Malformation (CV), Deficiency of Uridine Monophosphate Synthase (DP), and Mulefoot (MF). Brachyspina syndrome is a congenital inherited lethal defect in Holstein cattle that causes embryonic death, stillbirth and other deformities. (e.g., TY). Also included and provided for are methods to improve a herd by reducing the carriers of recessive genes comprising crossing an Animal of the present disclosure with dams of a herd having carriers of deleterious recessive genes.

As used herein, the term "HO840M003150607238 Genotype" or "Animal Genotype" provides for, and includes, diploid Bos taurus cell or a plurality of diploid Bos taurus cells comprising improved germplasm characterized by a genome having homozygous loci comprising 90% to 100% nucleic acid sequences selected from the group selected from SEQ ID NOs:1 to 2904829048. The present disclosure provides for, and includes, a diploid Bos taurus cell or a plurality of diploid Bos taurus cells comprising improved germplasm characterized by a genome having homozygous loci comprising 90% to 100% of the nucleic acid sequences selected from the group selected from SEQ ID NOs:1 to 2904829048. In an aspect, the diploid Bos taurus cell or a plurality of diploid Bos taurus cells comprise a genome having homozygous loci comprising at least 90% of the nucleic acid sequences selected from the group consisting of SEQ ID NOs: 1 to 2904829048. In an aspect, the genome of said Bos taurus cell or cells further comprise heterozygous loci comprising at least 90% of the nucleic acid sequences selected from the group consisting of SEQ ID NO: 29049 to 41648. In an aspect, the plurality of cells comprise a frozen vial, a cell culture, a tissue, a zygote, an embryo, a calf, or a mature adult. In some aspects, the Bos taurus cells are non-reproductive cells. In an aspect, the number of cells in a plurality of cells of the present disclosure is two or more, 100 or more, 1000 or more, $10^4$ or more, $10^5$ or more, or $10^6$ or more. In an aspect, the cells are in a container and comprise between $10^4$ and $10^7$ cells. In an aspect, the number of cells is between $10^5$ and $10^7$ cells.

In other aspects, the present disclosure provides for and includes, a diploid Bos taurus cell or a plurality of diploid Bos taurus cells comprising improved germplasm characterized by a genome comprising homozygous loci comprising at least 95% of the nucleic acid sequences selected from the group consisting of SEQ ID NOs: 1 to 29048. In an aspect, the diploid Bos taurus cell or plurality of diploid Bos taurus cells further comprise heterozygous loci comprising at least 95% of the nucleic acid sequences selected from the group consisting of SEQ ID NO: 17200 to 29806. In another aspect, the diploid Bos taurus cell or plurality of diploid Bos taurus cells comprise a genome comprising homozygous loci comprising at least 97% of the nucleic acid sequences selected from the group consisting of SEQ ID NOs:1 to 29048. In an aspect, the diploid Bos taurus cell or plurality of diploid Bos taurus cells further comprise heterozygous loci comprising at least 97% of the nucleic acid sequences selected from the group consisting of SEQ ID NO:17200 to 29806. In another aspect, the diploid Bos taurus cell or plurality of diploid Bos taurus cells comprise a genome comprising homozygous loci comprising at least 98% of the nucleic acid sequences selected from the group consisting of SEQ ID NOs:1 to 29048. In an aspect, the diploid Bos taurus cell or plurality of diploid Bos taurus cells further comprise heterozygous loci comprising at least 98% of the nucleic acid sequences selected from the group consisting of SEQ ID NO:17200 to 29806. In another aspect, the diploid Bos taurus cell or plurality of diploid Bos taurus cells comprise a genome comprising homozygous loci comprising at least 99% of the nucleic acid sequences selected from the group consisting of SEQ ID NOs:1 to 29048. In an aspect, the diploid Bos taurus cell or plurality of diploid Bos taurus cells comprise heterozygous loci comprising at least 99% of the nucleic acid sequences selected from the group consisting of SEQ ID NO:17200 to 29806. In another aspect, the diploid Bos taurus cell or plurality of diploid Bos taurus cells comprise a genome comprising homozygous loci comprising at least 99.5% of the nucleic acid sequences selected from the group consisting of SEQ ID NOs:1 to 29048. In an aspect, the diploid Bos taurus cell or plurality of diploid Bos taurus cells further comprise heterozygous loci comprising at least 99.5% of the nucleic acid sequences selected from the group consisting of SEQ ID NO:17200 to 29806. In an aspect, the diploid Bos taurus cell or plurality of diploid Bos taurus cells comprise a genome comprising homozygous loci comprising the nucleic acid sequences selected from the group consisting of SEQ ID NOs:1 to 29048. In an aspect, the diploid Bos taurus cell or plurality of diploid Bos taurus cells further comprise heterozygous loci comprising the nucleic acid sequences selected from the group consisting of SEQ ID NO:17200 to 29806. In an aspect, the diploid Bos taurus cells comprise Bos taurus variety HO840M003150607238, wherein a sample of cells of said variety has been deposited under ATCC Accession No. PTA-125702. As provided herein, the plurality of cells may comprise a frozen vial, a cell culture, a tissue, a zygote, an embryo, a calf, or a mature adult. In some aspects, the Bos taurus cells are non-reproductive cells. In an aspect, the number of cells in a plurality of cells of the present disclosure is two or more, 100 or more, 1000 or more, $10^4$ or more, $10^5$ or more, or $10^6$ or more. In an aspect, the cells are in a container and comprise between $10^4$ and $10^7$ cells. In an aspect, the number of cells is between $10^5$ and $10^7$ cells.

The present disclosure provides for, and includes, a diploid Bos taurus cell or a plurality of diploid Bos taurus cells comprising improved germplasm characterized by a genome comprising an Animal Genotype but that do not with favorable haplotypes for the traits comprise alleles selected from the group consisting of HHB, HHC, HHD, HEIM, HHR, HHP, HBR, and HDR.

The present disclosure provides for, and includes, tissue cultures comprising diploid Bos taurus cells comprising improved germplasm characterized by a genome comprising an Animal Genotype. In an aspect, the culture of Bos taurus cells comprise a genome comprising homozygous loci comprising the nucleic acid sequences selected from the group consisting of SEQ ID NOs:1 to 29048. As provided above, tissue cultures may comprise cells having 95% of the recited homozygous loci, 97% of the recited homozygous loci, 98% of the recited homozygous loci, 99% of the recited homozygous loci, 99.5% of the recited homozygous loci, and 100% of the recited homozygous loci, In an aspect, the diploid Bos taurus cells culture comprises Bos taurus variety HO840M003150607238, wherein a sample of cells of said variety has been deposited under ATCC Accession No. PTA-125702. As provided herein, the cell culture may be prepared from frozen cells or obtained as a primary culture from an embryo, a calf, or a mature adult. In certain aspects, the Bos taurus cells are non-reproductive cells.

Also included, and provided for, are Bos taurus cells that are haploid. As used herein, the term "HO840M003150607238 Haploid Genotype" or "Animal Haploid Genotype" provides for, and includes, a haploid Bos taurus cell or a plurality of haploid Bos taurus cells comprising improved germplasm characterized by a genome having loci comprising 90% to 100% of the nucleic acid sequences selected from the group selected from SEQ ID NOs:1 to 29048. As described below, haploid cells can be readily produced by somatic cell nuclear transfer of Bos taurus variety HO840M003150607238, from cells deposited under ATCC Accession No. PTA-125702. Mature animals prepared from variety HO840M003150607238 can be used to obtain haploid gametes through methods known in the art and discussed in detail below. As used herein, the term "gametes," "sperm," "spermatozoa," "spermatocyte," "spermatid," and "inseminate" are used interchangeable for haploid cells obtained from male animals and the terms will be understood by a person of ordinary skill in the art. Also as used herein, the term "gametes," "ova," "ovum," and "oocyte" are used interchangeable for haploid cells obtained from female animals. Haploid Bos taurus cells of the present disclosure comprise a haploid genome comprising a single copy of loci comprising at least 90% of the nucleic acid sequences selected from the group consisting of SEQ ID NOs:1 to 29048. Haploid cells of the present disclosure include a haploid genome comprising a single copy of loci comprising at least 95% of the nucleic acid sequences selected from the group consisting of SEQ ID NOs:1 to 29048. Haploid cells of the present disclosure also include a haploid genome comprising a single copy of loci comprising at least 97% of the nucleic acid sequences selected from the group consisting of SEQ ID NOs:1 to 29048. Haploid cells of the present disclosure may also comprise a haploid genome comprising a single copy of loci comprising at least 98% of the nucleic acid sequences selected from the group consisting of SEQ ID NOs:1 to 29048. Haploid cells of the present disclosure include a haploid genome comprising a single copy of loci comprising at least 99% of the nucleic acid sequences selected from the group consisting of SEQ ID NOs:1 to 29048. In some aspects, haploid cells of the present disclosure comprise a haploid genome comprising a single copy of loci comprising at least 99.5% of the nucleic acid sequences selected from the group consisting of SEQ ID NOs:1 to 29048. Haploid cells of the present disclosure also include cells comprising a haploid genome comprising a single copy of loci comprising the nucleic acid sequences selected from the group consisting of SEQ ID NOs:1 to 29048. In an aspect, the number of haploid cells in a plurality of cells of the present disclosure is 1000 or more, $10^4$ or more, $10^5$ or more, or $10^6$ or more. In an aspect, the cells are in a container and comprise between $10^4$ and $10^7$ cells. In an aspect, the number of cells in a container is between $10^5$ and $10^7$ cells.

As provided herein, the plurality of haploid cells may be cells in fresh semen. Methods for the collection of sperm from mature bulls are well known in the art.

Bos taurus germplasms are often provided as frozen (cryopreserved) semen samples. Long-term semen storage system is advantageous by allowing movement of artificial insemination (AI) doses throughout the world without compromising semen viability. Long-term storage also enables specific health checks to be carried out on both the semen and individual males thus minimizing the risk of the spread of disease through AI. Cryopreservation techniques for semen are well known to those skilled in the art.

As provided herein, useful cryoprotectants are not limited to those acting by a particular mechanism. In an aspect, the cryoprotectant acts, at least in part, by reducing intracellular dehydration. Not to be limited by theory, freezing is accompanied by an increase in solute concentration in the medium surrounding sperm that draws water out of the cells leading to increases in intracellular electrolyte concentration. Cryoprotectants of the present disclosure include, but are not limited to glycerol (GLY), 1,1,1-tris(hydroxymethyl)ethane [2-hydroxymethyl-2-methyl-propane-1,3-diol] (THE), 1,1,1-tris(hydroxymethyl)propane [2-ethyl-2-hydroxymethyl-propane-1,3-diol] (THP), ethylene glycol (EG), propane-1,2-diol (PD2), propane-1,3-diol (PD3) and dimethyl sulphoxide (DMSO), sucrose, trehalose, dextrose, raffinose, lactose, melibiose, melezitose, mannotriose, stachyose, dextran, hydroxy-ethyl starch, maltitol, lactitol, polyethyleneglycol, propylene glycol, polyvinvyl pyrrolidone, polyethylene oxide, and combinations thereof.

The present disclosure provides for, and includes, containers of Bos taurus inseminates comprising a plurality of sperm cells. Inseminates are prepared by combining fresh semen samples with a cryoprotectant and freezing the samples. Upon thawing, the sperm retain high levels of motility and fertility. In addition to the cryoprotectant, inseminates often include one or more additional components. In an aspect, the inseminate comprises $10^4$ or more, $10^5$ or more, or $10^6$ or more cells. In an aspect, the inseminate is provided in a container and comprise between $10^4$ and $10^7$ cells. In an aspect, the number of cells in the container is between $10^5$ and $10^7$ cells.

In general, about 5 ml to about 15 ml of semen is collected from a bull and optionally mixed with a suitable extender and cryoprotectant. For example, in an aspect, about 10 ml of semen is collected and mixed with about 240 ml of Triladyl™ solution, which is an off the shelf product that is available from Minitube of America in Verona, Wis. The Triladyl™ contains an extender and a cryoprotectant, such as glycerol. The mixture of semen, extender and cryoprotectant is then placed in plastic straws and frozen. In the industry the contents of the frozen straw is generally referred to as frozen semen, although it also contains an extender and a cryoprotectant. A goal is to cryopreserve about 20 million motile sperm in a ½ ml semen straw.

As used herein, an inseminate refers to a composition of Bos taurus sperm having an Animal Haploid Genotype and a cryoprotectant. Also provided are inseminates further comprising a component selected from the group consisting of an extender, an antibiotic, a buffer, an energy source, an antioxidant, and a protein source. Inseminates according to the present disclosure may be frozen or thawed.

The present specification provides for, and includes, inseminates comprising a sperm having a genome comprising an Animal Haploid Genotype. In an aspect, the inseminate comprises Bos taurus sperm comprising at least 90% of each of the recited loci. In an aspect, the inseminate comprises at least 95% of each of the loci. In an aspect, the inseminate comprises at least 97% of each of the loci. In an aspect, the inseminate comprises at least 98% of each of the loci. In an aspect, the inseminate comprises at least 99% of each of the loci. In an aspect, the inseminate comprises at least 99.5% of each of the loci. In an aspect, the inseminate comprises sperm cells from Bos taurus variety HO840M003150607238, wherein a sample of cells of said variety has been deposited under ATCC Accession No. PTA-125702. As provided herein, the inseminate may be fresh, frozen, or frozen and thawed and may further comprise component selected from the group consisting of an extender, an antibiotic, a buffer, an energy source, an antioxidant, and a protein source.

The present disclosure further provides for, and includes, Bos taurus inseminates comprising a sperm having a genome an Animal Haploid Genotype and further comprising one or more extenders. The term "extender" refers to any medium that extends to preserve sperm viability. The term "extension" refers to the dilution of sperm and cryoprotectant (e.g., an inseminate) with extender. An extender suitable for use in the selected sperm sample includes a physiologically acceptable carrier. The physiologically acceptable carrier is typically aqueous, and, in certain aspects, includes deionized water. Suitable extenders commonly comprise one or more of the following additional components: a component that maintains osmolality and buffers pH, an organic substance that prevents cold shock and preserves fertility of sperm, a detergent that acts synergistically with certain organic substances to enhance preservation of sperm, an energy source that can be readily utilized by sperm, an antioxidant, which protects sperm from cold shock. a substance that facilitates sperm capacitation, and one or more antibiotics. In aspects according to the present disclosure, the extender may be a commercial extender, such as BoviPRO® CryoGuard, BIOXcell, Cryobos®, Andromed®, Andromed® CSS, Triladyl®, Biladyl®, Steridyl®, and Biociphos. See for example U.S. Patent Publication No. 2003/0157475 published Aug. 21, 2003.

The present disclosure further provides for, and includes, Bos taurus inseminates comprising a sperm having a genome comprising an Animal Haploid Genotype and further comprising extenders that are a source of protein. Suitable protein sources include, but are not limited to egg yolk, milk, BSA and derivatives and combinations thereof. Inseminates comprising a protein source may further include one or more additional components selected from the group consisting of osmolytes, a buffer, and organic substances that prevent cold shock, detergents, energy sources, antioxidants, and one or more antibiotics.

The present disclosure further provides for, and includes, Bos taurus inseminates comprising a sperm having a genome comprising an Animal Haploid Genotype wherein the osmolality of the inseminate is controlled. The term "osmolality," as used herein, is a measure of the osmotic pressure of dissolved solute particles in an aqueous solution (e.g., an extender). The solute particles include both ions and non-ionized molecules. Osmolality is expressed as the concentration of osmotically active particles (i.e., osmoles) dissolved in 1 kg of water.

Substances helpful in maintaining osmolality and pH within these ranges are well known in the art and can be added to the extender as a solid or already in solution. A buffer containing a salt, a carbohydrate, or a combination thereof can be employed for this purpose. In aspects according to the present disclosure, the osmolality is between about 250 milliosmoles (mOsM) to about 350 mOsM. In certain aspects, the pH of the Bos taurus inseminate is between 6.9 and 7.5. Specific examples of osmolytes and buffers include sodium citrate, Tris[hydroxymethyl]aminomethane, and TES (N-Tris [Hydroxymethyl]methyl-2-aminoethanesulfonic acid), and monosodium glutamate buffers; milk; HEPES-buffered medium; and any combination thereof. The component employed to help maintain osmolality and provide buffering capacity in a particular application can vary depending on the other components of the extender and, in some cases, on the species from which the sperm are derived. The selection of such a component for use in the present invention is, however, within the level of skill in the art. Inseminates comprising an osmolyte may further include one or more additional components selected from the group consisting of a protein source, a buffer, and organic substances that prevent cold shock, detergents, energy sources, antioxidants, and one or more antibiotics.

The present disclosure further provides for, and includes, Bos taurus inseminates comprising a sperm having a genome comprising an Animal Haploid Genotype comprising extenders that comprise an antibiotic, since substantial bacterial growth can threaten sperm viability and increase the risk of infection of the host in artificial insemination or in vitro fertilization procedures. Any of a variety of antibiotics useful in the cryopreservation of cells can also be employed in the extender. The selection of a suitable antibiotic depends on the species from which the sperm was obtained, the procedures involved in obtaining and handling the sperm sample, and the specific microorganism(s) to be targeted. Exemplary antibiotics include tylosin, gentamicin, lincomycin, spectinomycin, linco-spectin (a combination of lincomycin and spectinomycin), penicillin, streptomycin, and ticarcillin, which can be used alone or in combination. However, one skilled in the art can readily determine other antibiotics suitable for use in the extender. Inseminates comprising an osmolyte may further include one or more additional components selected from the group consisting of a protein source, a buffer, and organic substances that prevent cold shock, detergents, energy sources, antioxidants, and osmolytes.

The present disclosure provides for, and includes Bos taurus inseminates comprising a sperm having a genome comprising an Animal Haploid Genotype and further comprising organic stress reducing agents. Organic stress reducing agents (OSR) provide improved motility, viability, fertility, and integrity of sperm cells in the Bos taurus inseminates of the present disclosure. Suitable OSRs include, but are not limited to catalase, superoxide dismutase (SOD), a SOD mimic, glutathione, glutathione reductase, glutathione peroxidase, pyruvate, mercaptoethanol, butylated hydroxytoluene (BHT), lipoic acid, flavins, quinines, vitamin K (and related vitamers), vitamin B12 (and related vitamers), vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof. Bos taurus inseminates and compositions according to the present disclosure can include one or more OSRs. Inseminates comprising a one or more OSRs may further include one or more additional components selected from the group consisting of a protein source, a buffer, and organic substances that prevent cold shock, detergents, energy sources, antioxidants, and osmolytes.

The present specification provides for, and includes, inseminates wherein the sperm have undergone one or more selections to prepare selected sperm inseminate. In certain aspects, selected sperm inseminates may be selected based on sex-type. In some aspects, the sperm are sex selected prior to preparing the selected sperm inseminate. In other aspects, the inseminate is prepared and then subjected to a sex-type selection processes. In aspects according to the present disclosure, the sex-type selection is performed prior to freezing the inseminate. In other aspects, the sex-type selection process is performed after thawing of a frozen inseminate.

Sex-type selection may be performed based on slight differences in the physical characteristics of sperm cells. Selection may also be performed based on nucleic acid sequence. A variety of methods are available for selecting cells including flow-cytometric methods. Importantly, the selection and subsequent processing of sperm creates challenges to maintain fertility and successful insemination when used in breeding. Methods of sex-type selection are known in the art.

The present disclosure provides for, and includes, sex selected inseminates comprising sperm having a genome comprising an Animal Haploid Genotype.

In an aspect, the sex selected inseminate comprises Bos taurus sperm comprising at least 90% of each of the recited loci. In an aspect, the sex selected inseminate comprises at least 95% of each of the recited loci. In another aspect, the sex selected inseminate comprises at least 97% of each of the recited loci. Other aspects provide sex selected inseminates comprising at least 98% of each of the recited loci. In an aspect, the sex selected inseminate comprises at least 99% of each of the recited loci. In a further aspect, the sex selected inseminate comprises at least 99.5% of each of the recited loci. In an aspect, the sex selected inseminate comprises sperm cells from Bos taurus variety HO840M003 150607238, wherein a sample of cells of said variety has been deposited under ATCC Accession No. PTA-125702. As provided herein, the sex selected inseminate may be fresh, frozen, or frozen and thawed and may further comprise one or more components selected from the group consisting of an extender, an antibiotic, a buffer, an energy source, an antioxidant, and a protein source. As provided herein, the sex selected inseminate may be skewed toward X-chromosome bearing or Y-chromosome bearing populations of spermatozoa. In an aspect, the sex selected inseminate comprises $10^4$ or more, $10^5$ or more, or $10^6$ or more cells. In an aspect, the sex selected inseminate is provided in a container and comprises between $10^4$ and $10^7$ cells. In an aspect, the number of sex selected cells in the container is between $10^5$ and $10^7$ cells.

The present disclosure provides for, and includes, a container of a Bos taurus inseminate comprising a plurality of sperm cells having attributes of Bos taurus semen variety HO840003150607238 wherein a sample of cells of said variety has been deposited under ATCC Accession No. PTA-125702.

The disclosure provides for, and includes, the distinguishing attributes of the inseminates of the present disclosure in Table 7. The unexpected and desirable combination of attributes is particularly valuable for dairy herd improvement and breeding purposes.

TABLE 7

Composite scores, linear trait scores and genomic results for HO840003150607238

| | Sex id17 | M HO840003150607238 |
|---|---|---|
| | Birth Date | 2018 Jun. 03 |
| TPI | TPI | 2905 |
| Net Merit Score | NM$ | 1131 |
| productive life | PL | 8.4 |
| somatic cell score | SCS | 2.57 |
| Daughter Pregnancy Rate | DPR | 1.2 |
| Cow Livability | LIV | 4.5 |
| PTA MILK | Milk | 1351 |
| PTAF | Fat | 127 |
| PTAP | Pro | 57 |
| Heifer Conception Rate | HCR | 2.5 |
| cow conception rate | CCR | 3.7 |
| STA dairy form | STA | −0.50 |
| Strength | STR | −0.72 |
| Body Depth | BDE | −0.87 |
| Dairy Form | DFM | 0.77 |
| Rump Angle | RPA | −0.61 |
| | TRW | −0.38 |
| | RLS | −1.15 |
| | RLR | 1.35 |
| Fore Udder Height | FTA | 0.43 |
| PTA Type | PTAT | 1.21 |
| Fore Udder Attachment | FUA | 1.42 |
| Rear Udder Height | RUH | 1.74 |
| Rear Udder Width | RUW | 1.60 |
| Udder Cleft | UCL | 0.84 |
| Udder Depth | UDP | 1.03 |
| Front Teat Placement | FTP | 0.95 |
| Teat Length | TLG | −2.20 |
| Feet Leg Score | FLS | 1.33 |
| Rear Teat Placement | RTP | 0.79 |
| Sire Calving Ease | SCE | 6.6 |
| Service Sire Stillbirth | SSB | 7.1 |
| Daughter Stillbirth | DSB | 3.9 |
| Daughter Calving Ease | DCE | 3.1 |
| Udder Composite Index | UDC | 1.42 |
| Feet & Legs Composite | FLC | 1.49 |
| TPI Formula | TPI | 2905 |
| Brachyspina/FANCI | HH0 | T |
| APAF1 | HH1 | T |
| — | HH2 | T |
| SMC2 | HH3 | T |
| GART | HH4 | T |
| — | HH5 | T |
| BLAD/ITGB2 | HHB | T |
| CVM/SLC35A3 | HHC | T |
| DUMPS/UMPS | HCD | 0 |
| Mulefoot/LRP4 | HHM | T |
| red color/MC1R | HRR | T |
| Polledness/POLLED | HHP | T |
| | HBR | T |
| | HDR | T |
| | naab_code | 29HO19060 |
| | Dam Name | ABS 7405 ACAPELLA-ET |
| | Sire | TORQUE |
| | MGS | YODER |
| | Milk Fever | −0.5 |
| | DAb | 0.2 |
| | Ketosis | 1.1 |
| | Mastitis | 2.0 |
| | Metritis | 3.0 |
| | Retained Placenta | 0.2 |

The present disclosure provides for, and includes, F1 progeny animals, and parts thereof comprising a diploid or haploid genome wherein the diploid genome comprises loci comprising 90% to 100% of the nucleic acid sequences selected from the group consisting of SEQ ID NOs:1 to 29048, and said F1 haploid genome having loci that comprise at least 25% of the nucleic acid sequences selected from the group consisting of SEQ ID NOs:1 to 29048. F1 progeny animals are obtained by crossing a first parent animal prepared by somatic cell nuclear transfer or breeding of the Bos taurus cells of the present application with a second parent.

F1 progeny animals obtained from crosses of Bos taurus animals having the Animal Genotype of the present application with elite DM animals (or SM animals for female germplasm) are likely to retain many loci in their homozygous state. Moreover, as nearly all elite DM (and SM) animals are genotyped, a breeder can predict prior to the cross whether progeny will share the desired loci and estimate the expected number of homozygous loci. In most aspects, these valuable F1 progeny are subsequently screened and the most desirable elite F1 progeny identified and selected for maintaining the DM (or SM herd) and for further improvement. Thus breeding strategies and decisions, informed by genomic data, can be made to continuously improve the germplasm and further, to lock in trait combinations by fixing homozygous alleles. Analysis and selection are necessary to not only make further improvements in breeding stock, but to maintain existing breeding stock quality. The animals of the present disclosure and those bred and selected from them do not occur naturally. Rather, under natural conditions, populations revert towards homogeneity. See Park et al., "Genome sequencing of the extinct Eurasian wild aurochs, Bos primigenius, illuminates the phylogeography and evolution of cattle," *Genome Biology* 16:234 (2015) Feral cattle (i.e., cattle not selected in breeding programs) are genetically distinct. See MacNeil et al., "Genetic relationships between feral cattle from Chirikof Island, Alaska and other breeds," *Animal Genetics* 38:193-197 (2007).

Thus, the present disclosure provides for, and includes, methods of breeding and selection to retain the homozygous alleles of Animal Genotype and generate new homozygous alleles from among the heterozygous loci selected from the group consisting of SEQ ID NO:29049 to 41648. In select crosses with elite second parents (e.g., a DM or SM second parent), selection of preferred traits comprising homozygous loci comprising at least 40% of the nucleic acid sequences selected from the group consisting of SEQ ID NOs:1 to 29067. Further, for an F1 progeny of Animal, the probability of any individual heterozygous locus becoming homozygous is either 50% when crossed with a second parent that is homozygous at a locus. When the second parent is heterozygous at a locus, there is a 25% probability of generating homozygosity at a locus. Thus, over time, the total number of homozygous loci will increase in select crosses.

Also provided for, and included in, the present disclosure, are F1 progeny animals that have desirable EBV or GEBV scores. Such animals are important Sires of females (SF) that are useful for breeding commercial herds and populations. Like breeding F1 progeny for the production of DM and SM animals, the second parent is a select parent, however it is not an elite parent. Select parents for the production of F1 progeny animals that are either SF or DF animals have positive EBV scores for one or more PTA traits selected from the group consisting of productive life (PL), somatic cell score (SCS), Daughter Pregnancy Rate (DPR), PTA MILK (Milk), PTAF (Fat), PTAP (Pro), and STA dairy form (STA).

As used herein, the term "HO840M003150607238 F1 Diploid Genotype" or "Animal F1 Diploid Genotype" provides for, and includes, a diploid F1 Bos taurus cells or a plurality of diploid Bos taurus cells comprising improved germplasm characterized by a genome having loci comprising 90% to 100% of the nucleic acids selected from the group selected from SEQ ID NOs:1 to 29048. In an aspect, an Animal F1 Diploid Genotype comprises at least 90% of the loci nucleic acid sequences selected from the group consisting of SEQ ID NOs:1 to 29048. In another aspect, an Animal F1 Diploid Genotype comprises at least 95% of the loci nucleic acid sequences selected from the group consisting of SEQ ID NOs:1 to 29048. In other aspects, an Animal F1 Diploid Genotype comprises at least 97% of the loci nucleic acid sequences selected from the group consisting of SEQ ID NOs:1 to 29048. In a further aspect, an Animal F1 Diploid Genotype comprising at least 97% of the loci nucleic acid sequences selected from the group consisting of SEQ ID NOs:1 to 29048. In yet a further aspect, an Animal F1 Diploid Genotype comprises at least 98% of the loci nucleic acid sequences selected from the group consisting of SEQ ID NOs:1 to 29048. In another aspect, an Animal F1 Diploid Genotype comprising at least 99% of the loci nucleic acid sequences selected from the group consisting of SEQ ID NOs:1 to 29048. In yet another aspect, an Animal F1 Diploid Genotype comprising at least 99.5% of the loci nucleic acid sequences selected from the group consisting of SEQ ID NOs:1 to 29048. In certain aspects, an F1 progeny animal of the present disclosure comprises an Animal F1 Diploid Genotype that comprises the nucleic acid sequences selected from the group consisting of SEQ ID NOs:1 to 29048. In an aspect, the F1 progeny animal, or part thereof, is an F1 progeny animal of Bos taurus variety HO840M003150607238, wherein a sample of cells of said variety has been deposited under ATCC Accession No. PTA-125702. As provided herein, the present specification provides for parts of F1 progeny animals including cells, cell cultures, and tissues. Also provided are frozen samples of parts of F1 progeny animals. Cells of F1 progeny animals include somatic cells and haploid germ cells (e.g., sperm and ova depending on the sex). In certain aspects, the Bos taurus cells of an F1 progeny animal are non-reproductive cells.

The present disclosure further provides for, and includes, F1 progeny animals, or parts thereof, further comprise a Net Merit index (NM$) of at least 1000 or a Total Performance Index (TPI) of at least 2000. In an aspect, the F1 progeny animals, or parts thereof, comprise a Net Merit index (NM$) of at least 800. In a further aspect, the F1 progeny animals, or parts thereof, comprise a Net Merit index (NM$) of at least 900.

The present disclosure further provides for, and includes, F1 progeny animals, or parts thereof, comprising a diploid genome comprising between homozygous loci at between 40% and 80% of the nucleic acid sequences selected from the group consisting of SEQ ID NOs:1 to 29048. In another aspect, the F1 progeny comprise homozygous loci at least 50% of the nucleic acid sequences selected from the group consisting of SEQ ID NOs:1 to 29048. In yet another aspect, the F1 progeny comprise homozygous loci at least 60% of the nucleic acid sequences selected from the group consisting of SEQ ID NOs:1 to 29048. In some crosses, the F1 progeny comprise homozygous loci at least 70% of the nucleic acid sequences selected from the group consisting of SEQ ID NOs:1 to 29048. In an aspect, F1 progeny can comprise homozygous loci at least 80% of the nucleic acid sequences selected from the group consisting of SEQ ID NOs:1 to 29048. In certain aspect, F1 progeny comprise between 60 and 80% of the nucleic acid sequences selected from the group consisting of SEQ ID NOs:1 to 29048 that are homozygous. In certain aspects, an animal having an Animal Genotype is crossed to a DM or SM animal, wherein said an F1 Animal comprises a genome having at least 90% of the loci comprising the nucleic acid sequences selected from the group consisting of SEQ ID NOs: 1 to 29048, and at least 45% of said loci are homozygous. In certain aspects, an animal having an Animal Genotype is crossed to a DM or SM animal, wherein said an F1 Animal comprises a genome having at least 95% of the loci comprising the nucleic acid sequences selected from the group consisting of SEQ ID NOs: 1 to 29048, and at least 55% of said loci are homozygous. In other aspects, an animal having an Animal Genotype is crossed to a DM or SM animal, wherein said an F1 Animal comprises a genome having at least 95% of the loci comprising the nucleic acid sequences selected from the group consisting of SEQ ID NOs: 1 to 29048, and at least 65% of said loci are homozygous. In certain aspects, the second parent is selected that comprises Net Merit index (NM$) of at least 1000, a Total Performance Index (TPI) of at least 2000 in any given progeny generation. In aspects of the present disclosure, the F1 progeny animals comprise a Net Merit index (NM$) of at least 1000 or a Total Performance Index (TPI) of at least 2000.

The present disclosure further provides for, and includes, methods to prepare improved F1 progeny animals comprising selecting a second parent having a Net Merit index (NM$) of at least 1000 or a Total Performance Index (TPI) of at least 2000. In an aspect, the second parent comprises a Net Merit index (NM$) of at least 800. In a further aspect, the second parent comprises a Net Merit index (NM$) of at least 900.

The present disclosure further provides for, and includes, F1 progeny that are F1 hybrid animals. As used herein, an F1 hybrid animal is an animal comprising an Animal Haploid Genotype and a haploid genome of an animal that is not a Holstein breed. In an aspect, the second parent of the hybrid a Bos indicus breed. In an aspect, the second parent is a member of a breed selected from the group consisting of Angus (ANG), Beef Shorthorn (SHR), Belgian Blue (BBL), Belted Galloway (BGA), Brahman (BRM), British Shorthorn (BSHN), Brown Swiss (BSW), Dutch Belted (DBE), Dutch Friesian(DFR), East Anatolian Red (EAR), English Longhorn (ELO), Finnish Ayrshire(FAY), French Brown Swiss (BRU), Galloway (GAL), Gascon (GAS), Guernsey (GNS), Hereford (HFD), Jersey (JER), Limousin (LMS), Longhorn (LHR), Milking Shorthorn (MSH), Normande (NOR), Norwegian Red (NRC), Red Angus (RGU), Texas Longhorn (TXL), Wagyu (WAG), and combinations of each.

In aspects according to the present disclosure, included are gametes obtained from F1 progeny of a first parent comprising a diploid genome comprising Animal Genotype and a second parent having a Net Merit index (NM$) of at least 1000 or a Total Performance Index (TPI) of at least 2000. In an aspect, the second parent comprises a Net Merit index (NM$) of at least 800. In a further aspect, the second parent comprises a Net Merit index (NM$) of at least 900. Crosses of Animal Genotype animals to improve select DM and SM animals, results in superior F1 animals having a having an Animal F1 Diploid Genotype. Improved F1 progeny having an Animal F1 Genotype that are produced from select DM animals having loci selected from the group selected from SEQ ID NOs:1 to 29048. Accordingly, in additional to the at least 90% of the loci comprising the nucleic acid sequences selected from the group consisting of SEQ ID NOs: 1 to 29048 provided by Animal, a DM animal provides loci comprising nucleic acids selected from the group consisting of SEQ ID NOs: 1 to 29048 provides for the generation of homozygous loci. In an aspect, the number of homozygous loci thus generated is at least 25%.

As used herein, the term "HO840M003150607238 F1 Haploid Genotype" or "Animal F1 Haploid Genotype" provides for, and includes, haploid Bos taurus cells or a plurality of haploid Bos taurus cells comprising improved germplasm characterized by a genome comprising between 25% and 100% of the loci selected from the group selected from SEQ ID NOs:1 to 29048. In aspects, an Animal F1 Haploid Genotype comprises between 25% and 45% of the loci selected from the group selected from SEQ ID NOs:1 to 29048. In aspects, the genome comprises at least 30% of the selected loci. In some aspects, the F1 haploid genotype comprises between 25 and 35% of the group of SEQ ID NOs.

In an aspect, the gametes of an F1 progeny animal of the present disclosure comprises an Animal F1 Haploid Genotype having at least 45% of the loci nucleic acid sequences selected from the group consisting of SEQ ID NOs:1 to 29048. In another aspect, the gamete of an F1 progeny animal of the present disclosure comprises an Animal F1 Haploid Genotype of at least 50% of the loci nucleic acid sequences selected from the group consisting of SEQ ID NOs:1 to 29048. In yet another aspect, the gamete of an F1 progeny animal of the present disclosure comprises an Animal F1 Haploid Genotype of at least 55% of the loci nucleic acid sequences selected from the group consisting of SEQ ID NOs:1 to 29048.

As provided herein, gametes of an F1 progeny animal comprise between 55% and 95% of the loci of an Animal F1 Haploid Genotype comprising nucleic acid sequences selected from the group consisting of SEQ ID NOs:1 to 29048. As will be understood by a persons of skill in the art, the smaller the phylogenetic distance between the first parent and second parent, the greater the probability of obtaining progeny having the desirable high levels of desirable loci. As discussed, given the availability of genomic data from a second parent, the expectation of obtaining F1 progeny have high number of homozygous loci can be determined and accordingly the probability of gametes having desired loci determined. In an aspect, gametes of an F1 progeny animal comprise 60% of the loci of the Animal F1 Haploid Genotype. In another aspect, gametes of an F1 progeny animal comprise 70% of the loci of the Animal F1 Haploid Genotype. In yet another aspect, gametes of an F1 progeny animal comprise 75% of the loci of the Animal F1 Haploid Genotype. Other aspects provide gametes of an F1 progeny animal that comprise 80% of the loci of the Animal F1 Haploid Genotype.

The present disclosure provides for, and includes, methods for improving bovine herds by selective breeding. Generally, selective breeding includes mating through natural service, artificial insemination, in vitro fertilization and embryo transfer. As provided herein, selective breeding comprises providing a bull of variety HO840003150607238, or a frozen inseminate thereof, to a second parent, artificially inseminating or inseminating by natural service, and calving a progeny calf. In an aspect, the selective breeding comprises providing an inseminate comprising a sperm having a genome comprising an Animal Haploid Genotype. In another aspect, the disclosure provides for, and includes, providing an F1 inseminate comprising a sperm having a genome comprising an Animal F1 Haploid Genotype. In certain aspects, the second parent is an animal of a herd in need of improvement. Herds in need of improvement generally comprise DF animals having NM$ scores below 900. In an aspect, a herd in need of improvement is commercial herd.

In aspects according to the present disclosure, methods of improving herds further includes testing a second parent for the haplotypes HHB, HHC, HHD, HHM, HBR, and HDR and selecting a second parent lacking one or more haplotypes HHB, HHC, HHD, HHM, HBR, or HDR.

The present disclosure provides for, and includes, a composition comprising a Bos taurus genome comprising an Animal Genotype as recited above. In an aspect, the Bos taurus genome further comprises heterozygous loci comprising at least 90% of the nucleic acid sequences selected from the group consisting of SEQ ID NO: 29049 to 41648. In an aspect, the composition comprises an isolated nucleus or plurality thereof, a cell or plurality thereof, isolated genomic DNA. In some aspects, the composition comprises a Bos taurus genome from a non-reproductive cell.

In other aspects, the present disclosure provides, for and includes, a composition comprising a Bos taurus genome of Animal Genotype. In another aspect, a composition comprises an Animal Haploid Genotype. In a further aspect, a composition comprises an F1 Diploid Genotype. In yet another aspect, a composition comprises an F1 Haploid Genotype. In an aspect, the composition comprises a Bos taurus genome of Bos taurus variety HO840M003150607238, wherein a sample of cells of said variety has been deposited under ATCC Accession No. PTA-125702.

The present disclosure provides for, and includes, a composition comprising a genome comprising an Animal Genotype or an Animal Haploid Genotype as described above but that do not with favorable haplotypes for the traits comprise alleles selected from the group consisting of HHB, HHC, HHD, HHM, HHR, HHP, HBR, and HDR.

The present disclosure provides for, and includes, containers of Bos taurus inseminate comprising a plurality of sperm cells, wherein said plurality of sperm cells have the attributes of Bos taurus variety HO840M003150607238, wherein a sample of cells of said variety has been deposited under ATCC Accession No. PTA-125702. The present specification provides for, and includes, containers of inseminates comprising a sperm having a genome comprising Animal Haploid Genotype. In an aspect, the containers of inseminate comprises Bos taurus sperm comprising at least 90% of each of the recited loci. In an aspect, the containers of inseminate comprises at least 95% of each of the loci. In an aspect, the containers of inseminate comprises at least 97% of each of the loci. In an aspect, the inseminate comprises at least 98% of each of the loci. In an aspect, the containers of inseminate comprises at least 99% of each of the loci. In an aspect, the inseminate comprises at least 99.5% of each of the loci. In an aspect, the containers of inseminate comprises sperm cells from Bos taurus variety HO840M003150607238, wherein a sample of cells of said variety has been deposited under ATCC Accession No. PTA-125702. As provided herein, the inseminate in the containers may be fresh, frozen, or frozen and thawed and may further comprise a component selected from the group consisting of an extender, an antibiotic, a buffer, an energy source, an antioxidant, and a protein source.

The present disclosure further provides for, and includes, containers of Bos taurus inseminates comprising a sperm having a genome comprising an Animal Haploid Genotype as recited above wherein the inseminate is free of recessive haplotype mutations for bovine leucocyte adhesion deficiency (BLAD; haplotype HHB), complex vertebral malformation (CVM; haplotype HHC), deficiency of uridine monophosphate synthase (DUMPS; haplotype HHD), and mulefoot (syndactyly; haplotype HHM), polledness (haplotype HHP), and red coat color (haplotypes HBR, HDR, and HEIR).

Also included are containers of inseminates comprising a sperm having an Animal Haploid Genotype as recited above wherein the sperm of the inseminate is obtained from a bull having a TPI of greater than 2900. In an aspect, the sperm in a container of inseminate is obtained from a bull having a TPI of greater than 2000. In another aspect, the sperm in a container of inseminate is obtained from a bull having a TPI of greater than 2100. In yet another the sperm in a container of inseminate is obtained from a bull having a TPI of greater than 2200. The specification further provides in an aspect, sperm in a container of inseminate obtained from a bull having a TPI of greater than 2300. In yet another aspect, the source of sperm has a TPI of greater than 2400. Other bulls having a TPI of greater than 2500 are further included. Also included are bulls having a TPI of greater than 2600 as sources of sperm of the containers of inseminates. In an aspect, containers of inseminates comprising a sperm having an Animal Haploid Genotype as recited above wherein the sperm of the inseminate is obtained from a bull having a TPI of greater than 2700. In an aspect the TPI of bulls suitable for the inseminates of the present specification range from 2100 to 2900.

The present disclosure provides for, and includes, processes for storing spermatozoa comprising obtaining a Bos taurus ejaculate spermatozoa, each spermatozoa having an Animal Haploid Genotype as recited above, mixing the Bos taurus ejaculate with a composition that induces sperm immotility and an antibiotic to form a sperm dispersion. In an aspect, the Bos taurus ejaculate is an ejaculate of a bull of Bos taurus variety HO840M003150607238, wherein a sample of cells of said variety has been deposited under ATCC Accession No. PTA-125702. In another aspect, the spermatozoa comprise an Animal F1 Haploid Genotype as recited above. In another aspect, the spermatozoa comprise an Animal F1 Haploid Genotype comprising at least 55% of the recited nucleic acid sequences. In another aspect, the spermatozoa comprise an Animal F1 Haploid Genotype comprising at least 60% of the recited nucleic acid sequences. In yet another aspect, the spermatozoa comprise an Animal F1 Haploid Genotype comprising at least 65% of the recited nucleic acid sequences. In yet another aspect, the spermatozoa comprise an Animal F1 Haploid Genotype comprising at least 70% of the recited nucleic acid sequences. In other aspects, the spermatozoa comprise an Animal F1 Haploid Genotype comprising at least 75% of the nucleic acid sequences. Other aspects provide for spermatozoa comprising an Animal F1 Haploid Genotype comprising at least 80% of the nucleic acid sequences. Further aspects provide for spermatozoa comprising an Animal F1 Haploid Genotype comprising at least 85% of the recited nucleic acid sequences. In addition, the disclosure provides spermatozoa comprising an Animal F1 Haploid Genotype comprising at least 90% of the recited nucleic acid sequences. Other aspects provide for obtaining a Bos taurus ejaculate comprising spermatozoa comprising an Animal F1 Haploid Genotype comprising at least 95% of the recited nucleic acid sequences. Further aspects provide for spermatozoa comprising an Animal F1 Haploid Genotype comprising at least 99% of the nucleic acid sequences selected from the group consisting of SEQ ID NOs:1 to 17199. As provided herein, the sperm dispersions may further comprise one or more components selected from the group consisting of a cryoprotectant, an extender, an antibiotic, a buffer, an energy source, an antioxidant, and a protein source. In aspects of the present disclosure, the number of cells in a sperm dispersion comprise 1000 or more, $10^4$ or more, $10^5$ or more, or $10^6$ or more cells. In an aspect, the cells are in a container and comprise between $10^4$ and $10^7$ cells. In an aspect, the number of cells is between $10^5$ and $10^7$ cells.

The process for storing spermatozoa further includes preparing a straw or sheath having a volume of sperm dispersion and freezing the sperm dispersion containing straw prior to storing. In an aspect, the volume of sperm dispersion is 0.25 milliliters (ml), 0.50 ml, or any volume between 0.1 and 1 ml. As provided by the present specification, the storing comprises maintaining the sperm dispersion at a temperature of −196° C. Also included, and provided for, in the process for storing spermatozoa is sorting said spermatozoa into X-chromosome or Y-chromosome enriched inseminate. In certain aspects, the process may further comprise removing immotile spermatozoa. In aspects of the present disclosure, the number of cells in a straw, sheath or container comprises between $1 \times 10^6$ to $100 \times 10^6$ cells. In an aspect, the cells are in a straw, sheath or container and comprise between $10^4$ and $10^7$ cells. In an aspect, the number of cells in straw, sheath or container is between $10^5$ and $10^7$ cells.

The present disclosure provides for, and includes a combination comprising an elongated container for use in the insemination of a Bos taurus dam and a sperm dispersion comprising a plurality of sperm, each sperm comprising a genome comprising an Animal Haploid Genotype or an Animal F1 Haploid Genotype, wherein said sperm dispersion comprises immotile spermatozoa and a composition that induces sperm immotility, and wherein the sperm dispersion is contained in the elongated container. In an aspect, the concentration of spermatozoa in the sperm dispersion is between about $0.04 \times 10^6$ sperm/ml to about $12 \times 10^7$ sperm/ml. In an aspect, the composition that induces sperm immotility comprises potassium and optionally sodium, the molar ratio of potassium to sodium being greater than 1:1, respectively. In an aspect, the composition that induces sperm immotility comprises potassium and optionally sodium, the molar ratio of potassium to sodium being greater than 1.75 to 1.0. Also provided for in the combination are sperm dispersions comprising a source of carbonate. In an aspect, the source of carbonate comprises $NaHCO_3$, $KHCO_3$, and $C_6H_8O_7$. In an aspect, the sperm dispersions comprise a buffer comprising 0.097 moles/L of $NaHCO_3$, 0.173 moles/L of $KHCO_3$, and 0.090 moles/L $C_6H_8O_7 \cdot H2O$ in water.

The present disclosure provides for, and includes, methods of inseminating a Bos taurus dam comprising thawing a frozen inseminate comprising a plurality of sperm cells, each sperm cell having a genome an Animal Haploid Genotype or an Animal F1 Haploid Genotype and artificially inseminating a dam with said thawed inseminate to produce an F1 bovine calf or an F2 bovine calf respectively. In an aspect, the method includes providing a plurality of sperm cells that comprise an Animal Haploid Genotype or an Animal F1 Haploid Genotype comprising at least 55% of the recited nucleic acid sequences. In another aspect, the method includes providing a plurality of sperm cells that comprise an Animal Haploid Genotype or an Animal F1 Haploid Genotype comprising at least 60% of the recited nucleic acid sequences. In yet another aspect, the method includes providing a plurality of sperm cells that comprise an Animal Haploid Genotype or an Animal F1 Haploid Genotype comprising at least 65% of the recited nucleic acid sequences. In yet another aspect, the method includes providing a plurality of sperm cells that comprise an Animal Haploid Genotype or an Animal F1 Haploid Genotype comprising at least 70% of the recited nucleic acid sequences. In other aspects, the method includes providing a plurality of sperm cells that comprise an Animal Haploid Genotype or an Animal F1 Haploid Genotype comprise at least 75% of the nucleic acid sequences. Other aspects of the method provide for sperm cells comprising an Animal Haploid Genotype or an Animal F1 Haploid Genotype comprising at least 80% of the nucleic acid sequences. Further aspects provide sperm cells comprising an Animal Haploid Genotype or an Animal F1 Haploid Genotype comprising at least 85% of the recited nucleic acid sequences. In addition, the methods provide sperm cells comprising an Animal Haploid Genotype or an Animal F1 Haploid Genotype comprising at least 90% of the nucleic acid sequences. Other aspects provide a frozen inseminate prepared from a Bos taurus ejaculate comprising spermatozoa comprising an Animal Haploid Genotype or an Animal F1 Haploid Genotype comprising at least 95% of the recited nucleic acid sequences. Further aspects provide for sperm cells comprising an Animal Haploid Genotype or an Animal F1 Haploid Genotype comprising at least 99% of the recited nucleic acid sequences. As provided herein, the inseminate suitable for the methods of insemination may further comprise one or more components selected from the group consisting of a cryoprotectant, an extender, an antibiotic, a buffer, an energy source, an antioxidant, and a protein source.

The present disclosure provides for, and includes, methods for preparing transgenic animals. Also provided for, and included, are transgenic animals having an Animal Genotype and an Animal F1 Diploid Genotype as recited above. Also included, and provided for, are haploid cells comprising a transgene comprising an Animal Haploid Genotype and an Animal F1 Haploid genotype as recited above.

As used herein, "transgenic animal, cell or tissue" includes reference to animals which comprises within its genome a gene encoding a heterologous polynucleotide. Generally, the gene is stably integrated within the genome such that the expression of the polynucleotide is passed on to successive generations. The gene may be integrated into the genome alone or as part of a recombinant expression cassette. "Transgenic" is used herein to include any cell, cell line, tissue, or organ, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extrachromosomal) by conventional breeding methods or by naturally occurring events such as random cross-fertilization, non-recombinant viral infection, non-recombinant bacterial transformation, non-recombinant transposition, or spontaneous mutation. The transgene can be introduced into the genomes of the present disclosure directly or through breeding with a transgene containing animal. Methods to prepare transgenic animals are known in the art, for example by pronucleus injection as described by Gordon et al., "Genetic transformation of mouse embryos by microinjection of purified DNA. Proc. Natl. Acad. Sci. USA 77:7380-7384 (1980). Pronucleus injection has been shown to be suitable for large domestic animals including pigs and cattle. See Hammer et al., "Production of transgenic rabbits, sheep and pigs by microinjection," Nature 315: 680-683 (1985) and Niemann, "Transgenic pigs expressing plant genes," Proc Natl Acad Sci USA 101:7211-7212 (2004). Other methods of generating transgenic animals are known in the art. See Park, et al., "Role of stem cells in large animal genetic engineering in the TALENs-CRISPR era," Reprod Fertil Dev 26:65-73 (2013).

Also provided, for and included, are gene edited animals having an Animal Genotype. Gene edited animals are non-transgenic animals. The animals of the present disclosure can be gene-edited animals having an Animal Genotype, an Animal F1 Diploid Genotype, an Animal Haploid Genotype and an Animal F1 Haploid genotype as recited above. Suitable methods for gene editing are known in the art. Methods include, but are not limited to, the methods provided in International Patent Publication No. WO 2015/148761 published Oct. 1, 2015, U.S. Pat. No. 9,868,962, published Jan. 16, 2018, and International Patent Publication No. WO 2017/132239 published Mar. 8, 2017, and references cited therein, all of which are incorporated by reference.

The following are non-limiting exemplary embodiments of the present disclosure:

1. The present disclosure provides for a plurality of Bos taurus cells comprising each cell having a genome comprising homozygous loci comprising at least 90% of the nucleic acid sequences selected from the group consisting of SEQ ID NOs:1 to 29048.
2. The plurality of Bos taurus sperm cells according to embodiment 1, further comprising heterozygous loci comprising at least 90% of the nucleic acid sequences selected from the group consisting of SEQ ID NO: 29049 to 41648.
3. The plurality of Bos taurus cells according to embodiment 1 or 2, wherein said cells comprise a frozen vial, a cell culture, a tissue, a zygote, an embryo, a calf, or a mature adult.
4. A plurality of Bos taurus gamete cells comprising at least 90% of the loci comprising the nucleic acid sequences selected from the group consisting of SEQ ID NOs:1 to 29048.
5. The plurality of Bos taurus gamete cells according to embodiment 4, wherein said gamete cells are cryopreserved.
6. The plurality of Bos taurus cells according to embodiment 4 or 5, wherein said cells comprise a cryopreserved bovine inseminate or a cryopreserved oocyte.
7. An F1 Bos taurus animal, or part thereof, said F1 Bos taurus animal comprising a genome comprising at least 90% of the loci comprising the nucleic acid sequences selected from the group consisting of SEQ ID NOs: 1 to 29048.
8. The F1 Bos taurus animal, or part thereof, according to embodiment 7, wherein said genome comprises the haploid genome of a parent Bos taurus animal having a Net Merit Index (NM$) of at least 1000.
9. The F1 Bos taurus animal, or part thereof, according to embodiment 7 or 8, wherein said F1 Bos taurus animal is prepared by artificial conception.
10. The F1 Bos taurus animal, or part thereof, according to any one of embodiments 7 to 9, wherein said artificial conception is in vitro fertilization and implantation, Artificial Insemination (AI), or in vivo insemination and embryo transfer (ET).
11. The F1 Bos taurus animal, or part thereof, according to any one of embodiments 7 and 10, wherein said part thereof is an isolated oocyte or a plurality of sperm.
12. The F1 Bos taurus animal, or part thereof, according to any one of embodiments 7 to 11, wherein said plurality of sperm comprise a genome comprising at least 45% of the loci comprising the nucleic acid sequences selected from the group consisting of SEQ ID NOs: 1 to 29048.

13. A Bos taurus inseminate composition comprising a cryoprotectant and semen of Bos taurus variety HO840M003150607238, wherein a sample of cells of said variety has been deposited under ATCC Accession No. PTA-125702.

14. An F1 Bos taurus inseminate comprising at least half of a haploid genome of Bos taurus variety HO840M003150607238, wherein a sample of cells of said variety has been deposited under ATCC Accession No. PTA-125702.

15. The F1 Bos taurus inseminate according to embodiment 14, wherein said inseminate comprises an F1 Haploid Genotype comprising 25% and 50% of the loci selected from the group selected from SEQ ID NOs:1 to 29048.

16. A Bos taurus animal, or part thereof, comprising one or more cells having at least 25% of the loci comprising nucleic acid sequences selected from the group consisting of SEQ ID NOs:1 to 29048.

17. The Bos taurus animal, or part thereof, according to embodiment 16, wherein said loci are obtainable from Bos taurus variety HO840M003150607238, wherein a sample of cells of said variety has been deposited under ATCC Accession No. PTA-125702.

18. The Bos taurus animal, or part thereof, according to any one of embodiments 16 or 17, prepared by crossing a bull of Bos taurus variety HO840M003150607238, wherein a sample of cells of said variety has been deposited under ATCC Accession No. PTA-125702 with a second parent to obtain an F1 progeny animal and crossing said F1 progeny animal with a second parent, and obtaining a Bos taurus animal comprising at least 25% of the loci comprising nucleic acid sequences selected from the group consisting of SEQ ID NOs: 1 to 29048.

19. The Bos taurus animal, or part thereof, according to any one of embodiments 16 to18, wherein said second parent has a Net Merit score (NM$) of at least 1000 or Total Performance Index (TPI) of at least 2000.

20. A plurality of Bos taurus cells, each comprising a diploid or haploid genome
each diploid genome comprising homozygous loci comprising at least 90% of the nucleic acid sequences selected from the group consisting of SEQ ID NOs: 1 to 29048; and
each haploid genome comprising at least 90% of the loci comprising the nucleic acid sequences selected from the group consisting of SEQ ID NOs: 1 to 29048.

EXAMPLES

Example 1: Genomic Characterization of Bos Taurus Cells

The genotype of HO840003150607238 was determined using the Illumina Infinium HTS BeadChip microarray system using the BovineSNP50 v3 BeadChip microarray kit (BeadChip) according to manufacturer's instructions. The BeadChip contains 53,714 highly informative SNP probes uniformly distributed across the entire genome of major cattle breed types at a median spacing of 37.4 kb. The SNP probes are validated in 18 common beef and dairy breeds. The BeadChip is a collaboration of Illumina, the USDA-ARS, the University of Missouri, and the University of Alberta. More than 22,000 SNP probes target novel SNP loci found in pooled populations of economically important beef and dairy cattle. The BeadChip is well known and extensively used by those of skill in the art. Other suitable genotyping chips and technologies can be used, including but not limited to the GeneSeek® Genomic Profiler™ High-Density array (GGP HD150K) and the Neogen GGP Bovine 50 k chip that contain 139376 and 47843 SNPs respectively (Neogen Genomics, Lincoln Nebr.).

A wide variety of publically available resources are known in the art including the bovine reference genome (Bovine Genome Sequencing and Analysis Consortium. "The genome sequence of taurine cattle: a window to ruminant biology and evolution. Science 324(5926):522-8), Btau (available at ftp(dot)hgsc(dot)bcm.tmc.edu/pub/data/Btaurus/fasta), and the Bovine HapMap Consortium data set (Bovine HapMap Consortium, "Genome-wide survey of SNP variation uncovers the genetic structure of cattle breeds," Science 324(5926):528-32 (2009) available on the internet at bovinehapmap(dot)org). Analysis tools and sequence data are maintained by the Bovine Genome Database (BGD) that is supported by the European Union's Seventh Framework Programme for research, technological development and demonstration (Grant Agreement No. 613689), and the USDA National Institute of Food and Agriculture. BGD is hosted at the University of Missouri.

TABLE 8

BovineSNP50 BeadChip Sources

| Source | BovineSNP50 v1 Probes | BovineSNP50 v2 Probes | BovineSNP50 v3 Probes |
| --- | --- | --- | --- |
| Novel SNPs [a] | 23,840 | 24,181 | 22,299 |
| Bovine HapMap Data Set | 12,298 | 12,342 | 11,607 |
| Btau Assembly SNPs | 9361 | 9404 | 9086 |
| Whole-Genome Shotgun Reads [b] | 5808 | 6038 | 5485 |
| Holstein BAC Sequence | 1409 | 1411 | 1238 |
| Parentage | 116 | 120 | 200 |
| Other | 1169 | 1113 | 3384 |
| Total | 54,001 | 54,609 | 53,218 |

[a] Derived from sequencing common cattle breeds using the Illumina GenomeAnalyzer.
[b] Obtained from six breeds: Norwegian Red, Holstein, Brahman, Angus, Jersey, and Limousin.

Example 2: Breeding and Selection of HO840003150607238

HO840003150607238 is a progeny animal of a breeding program for the improvement of dairy herds and breeding purposes. HO840003150607238 has the predicted characteristics as provided above in Table 7. The definitions and abbreviations are provided above. HO840003150607238 is an individual of the Holstein breed.

HO840003150607238 is a cross between Sire HO840003135669665 ("Sire") born on Sep. 24, 2016, and Dam HO840003128557405 ("Dam") born on Sep. 16, 2015. The composite scores and linear trait results of Sire and Dam are provided below in Table 9. The genotypes of Sire and Dam are provide above in Table 2 and Table 3. Like HO840003150607238, Sire and Dam are SM and DM animals respectively. Sire comprises homozygous loci comprising the nucleic acid sequences selected from the group consisting of SEQ ID NOs: 41674 to 57882 and heterozygous loci comprising the nucleic acid sequences selected from the group consisting of SEQ ID NOs: 57883 to 71267. Dam comprises homozygous loci comprising the nucleic acid sequences selected from the group consisting of SEQ ID NOs: 82237 to 98750 and heterozygous loci comprising the nucleic acid sequences selected from the group consisting of SEQ ID NOs: 98751 to 122665.

Sire is the progeny of paternal grand-Sire HOUSA000070726929 and paternal grand-Dam HOUSA000072292872. Dam is the progeny of maternal grand-Sire HOUSA000072128216 and maternal grand-Dam HOUSA000072852291. Notably, selective breeding has increased the sire NM$ from below about 950 to over 1100 in HO840003150607238. Other desirable traits are similarly improved.

The genomes, composite traits and other characteristics of the parents and grand-parents are determined using the methods of Example 1 and the results presented below in Table 10.

TABLE 9

Genomic Report for Parents of HO840003150607238

| Sex | Male | Female |
|---|---|---|
| id17 | HO840003138277108 | HO840003127335731 |
| Animal Name | TORQUE | ABS 7405 ACAPELLA-ET |
| Birth Date | 2016 Sep. 24 | 2015 Sep. 16 |
| NM$ | 953 | 1041 |
| PL | 7.9 | 7.5 |
| SCS | 2.49 | 2.85 |
| DPR | 2.8 | 2.8 |
| LIV | 4.6 | 3.5 |
| Milk | 1303 | 1083 |
| Fat | 92 | 120 |
| Pro | 49 | 48 |
| HCR | 1.8 | 4.5 |
| CCR | 4.0 | 5.1 |
| STA | 0.18 | -0.75 |
| STR | -0.66 | -0.45 |
| BDE | -1.00 | -0.70 |
| DFM | -0.12 | 0.84 |
| RPA | 0.66 | -0.11 |
| TRW | -0.40 | -0.31 |
| RLS | -0.67 | -1.56 |
| RLR | 0.42 | 1.27 |
| FTA | 0.43 | 0.12 |
| PTAT | 0.67 | 1.11 |
| FUA | 1.17 | 1.33 |
| RUH | 1.36 | 2.17 |
| RUW | 1.25 | 2.00 |
| UCL | 0.45 | 0.13 |
| UDP | 1.59 | 0.47 |
| FTP | 0.33 | 0.01 |
| TLG | -1.16 | -1.75 |
| FLS | 0.75 | 0.85 |
| RTP | 0.07 | -0.09 |
| SCE | 7.2 | 5.8 |
| SSB | 6.5 | 6.4 |
| DSB | 3.0 | 4.1 |
| DCE | 3.0 | 3.6 |
| UDC | 1.14 | 1.41 |
| FLC | 0.69 | 1.13 |
| TPI | 2714 | 2811 |
| HH0 | T | T |
| HH1 | T | T |
| HH2 | T | T |
| HH3 | T | T |
| HH4 | T | T |
| HH5 | T | C |
| HHB | T | T |
| HHC | T | T |
| HCD | 0 | 0 |
| HHP | T | T |
| HHR | T | T |
| naab_code | 029HO18634 | n/a |
| Dam Name | BUSH-BROS FAIRFAX 5290 | COMPASS-TRT AMRC AE J925-ET |
| Sire | SKYFALL | YODER |
| MGS | FAIRFAX | ALTAEMBASSY |

TABLE 9-continued

Genomic Report for Parents of HO840003150607238

| MilkFever | -0.3 | -0.5 |
|---|---|---|
| DAb | 0.1 | 0.5 |
| Ketosis | 1.2 | 1.6 |
| Mastitis | 2.1 | 0.2 |
| Metritis | 2.4 | 2.9 |
| RetainedPlacenta | 0.1 | 0.1 |

TABLE 10

Genomic Report for Grand Parents of HO840003150607238

| Sex | Paternal Grand Sire | Paternal Grand Dam | Maternal Grand Sire | Maternal Grand Dam |
|---|---|---|---|---|
| id17 | HOUSA00 0070726929 | HOUSA00 0072292872 | HOUSA00 0072128216 | HOUSA00 0072852291 |
| Animal Name | UECKER SUPERSIRE JOSUPER-ET | MELARRY SHOTGLASS FRAZZLE | MR MOGUL DELTA 1427-ET | DE-SU SUPERSIRE 3349-ET |
| Birth Date | 2014 Nov. 17 | 2015 Jan. 28 | 2013 Jan. 05 | 2013 Sep. 30 |
| NM$ | 938 | 691 | 904 | 758 |
| PL | 6.2 | 6.7 | 5.2 | 5.3 |
| SCS | 2.61 | 2.55 | 3.04 | 2.72 |
| DPR | 1.4 | 2.7 | 1.8 | 0.8 |
| LIV | 3.2 | 3.5 | 0.6 | 2.8 |
| Milk | 1780 | 1011 | 1171 | 1208 |
| Fat | 107 | 52 | 105 | 89 |
| Pro | 56 | 39 | 51 | 45 |
| HCR | 2.0 | 0.8 | 3.9 | 1.6 |
| CCR | 2.5 | 3.3 | 4.3 | 1.7 |
| STA | 1.35 | -0.13 | 0.50 | 0.43 |
| STR | 0.60 | -0.27 | -0.02 | 0.20 |
| BDE | 0.28 | -0.92 | -0.11 | -0.19 |
| DFM | 0.88 | -0.92 | 1.34 | 0.71 |
| RPA | -0.25 | 1.05 | 1.84 | -0.94 |
| TRW | 0.47 | -0.38 | 0.14 | 0.79 |
| RLS | 0.10 | -1.80 | -2.61 | -0.28 |
| RLR | 1.01 | 1.12 | 2.27 | 0.44 |
| FTA | 1.43 | 0.88 | 0.84 | 0.32 |
| PTAT | 1.79 | 0.22 | 1.86 | 1.13 |
| FUA | 1.62 | 0.99 | 2.19 | 1.31 |
| RUH | 2.43 | 0.80 | 3.32 | 2.08 |
| RUW | 2.24 | 0.74 | 3.05 | 1.91 |
| UCL | 1.32 | -0.40 | 0.60 | 0.89 |
| UDP | 1.55 | 1.27 | 1.25 | 1.18 |
| FTP | 0.73 | -0.37 | 1.68 | -0.56 |
| TLG | -1.55 | 0.12 | -3.06 | 0.64 |
| FLS | 1.39 | 0.84 | 1.54 | 0.40 |
| RTP | 0.59 | -0.45 | 1.41 | -0.07 |
| SCE | 9.2 | 6.3 | 5.9 | 8.6 |
| SSB | 8.0 | 6.3 | 5.9 | 8.4 |
| DSB | 3.5 | 4.4 | 3.7 | 5.9 |
| DCE | 3.6 | 3.4 | 3.4 | 5.9 |
| UDC | 1.55 | 0.77 | 2.06 | 1.37 |
| FLC | 1.16 | 1.03 | 1.69 | 0.36 |
| TPI | 2774 | 2421 | 2730 | 2511 |
| HH0 | T | T | T | T |
| HH1 | T | T | T | T |
| HH2 | T | T | T | T |
| HH3 | T | T | T | T |
| HH4 | T | T | T | T |
| HH5 | T | T | T | C |
| HHB | T | T | T | T |
| HHC | T | T | T | T |
| HCD | 0 | 0 | 0 | 0 |
| HHP | T | T | T | T |
| HHR | T | T | T | T |
| naab_code | 029HO17918 | | 007HO12266 | |
| Dam Name | DE-SU MCCUTC HEN 2352-ET | BUSH-BROS SUPERSIRE 4624-ET | WOODCREST PLANET YAKARA-ET | SEAGULL-BAY MISS AMERICA-ET |

TABLE 10-continued

Genomic Report for Grand Parents of HO840003150607238

| Sire | JOSUPER | FAIRFAX | MOGUL | ALTAEMB ASSY |
|---|---|---|---|---|
| MGS | MCCUTC REN | SUPERSIRE | PLANET | ROBUST |
| MilkFever | −0.3 | −0.2 | −0.4 | −0.5 |
| DAb | 0.4 | 0.6 | 0.5 | 0.1 |
| Ketosis | 1.2 | 1.6 | 1.5 | 0.7 |
| Mastitis | 1.2 | 2.2 | −1.3 | 2.0 |
| Metritis | 1.9 | 2.7 | 2.8 | 1.5 |
| RetainedPlacenta | 0.1 | 0.0 | 0.1 | 0.0 |

Example 3: Culture of Bos Taurus Cells

Adult Bos taurus fibroblast cultures are established from ear punch or tail clip from HO840003150607238 at an age of less than one year according to standard methods.

Briefly, an ear punch or tail clip is treated with collagenase and digested. The collagenase treated cells are they collected by centrifugation and washed with buffered saline. The washed cells are treated with trypsin and triturated and a suspension of cells plated on standard culture dishes and cultured under standard conditions to prepare a primary culture. The cells are cultured and either fed or split 1:4 to 1:6 and the culture expanded. Cells are harvested when the culture reaches at least 10 million. At confluence, cells are collected by trypsin/EDTA treatment and centrifugation. Cells are resuspended and counted and then collected and resuspended a concentration of $1\times10^6$-$10^7$/mL. Cells are diluted with freezing medium (90% FBS+10% DMSO). Tubes are transferred to −80° C. overnight before being placed in liquid nitrogen for long term storage. A representative sample of culture prepared using these methods was deposited to the American Tissue Type Collection (ATCC) under Accession No. PTA-125702 on Feb. 21, 2019. The address for the ATCC is 10801 University Boulevard, Manassas, Va. 20110-2209.

Example 4: Somatic Cell Nuclear Transfer (SCNT) of Animal Cells

Somatic cell nuclear transfer (SCNT) is performed according the method of Ross and Cibelli, "Bovine Somatic Cell Nuclear Transfer," *Methods Mol Biol.* 636. 155-77 (2010). See also U.S. Pat. No. 6,011,197 issued Jan. 4, 2000, to Strelchenko et al.

Briefly, five to seven days before performing SCNT, a culture of fibroblasts as described in Example 3 are plated in four well dishes at a density of 100,000 cells per well and cultured. The cells are synchronized in the G0 stage by contact inhibition. Oocytes are harvested from either slaughterhouse-derived ovaries or from live animals by ultrasound-guided oocyte aspiration. The oocytes are matured in vitro and enucleated. The cultured fibroblasts are injected in to enucleated oocytes and oocyte-cell fusion is induced using a square DC pulse generator. Fused oocytes are activated using ionomycin and cultured under standard conditions. At 48 h after activation, noncleaved embryos removed from culture and at 72 h after activation, the culture medium is supplemented with serum and cultured for seven days before being recovered and implanted in synchronized recipients. Calves are born normally to the surrogate mother and are genetically identical offspring to Animal. In addition to providing a source of inseminate for herd improvement, new cultures of cells as described in Example 1 can be prepared. The high availability of bovine oocytes and the relatively higher efficiency levels usually obtained in cattle provide for the use of SCNT for both commercial and research purposes.

Example 5: Breeding of Animal Progeny

Mature bulls prepared by the methods of the present specification are used for breeding purposes using conventional artificial insemination methods. Alternatively, bulls prepared by SCNT can be used for natural service.

Frozen inseminate obtained as provided below in Example 7 is provided for artificial insemination for the improvement of existing herds. Breeding for the improvement of existing herds does not generally require consideration of the recipient heifer or cow. In an aspect, a Dam is selected from a herd in need of improvement and artificially inseminated with Animal inseminate. In an aspect, a herd in need of improvement has an average NM$ index of less than 700. In an aspect, a herd in need of improvement has an average NM$ index of between 700 and 1000. After gestation, calves are born and evaluated for production, composite traits, and predicted transmitting abilities. In some cases, genomic testing is performed. The resulting calves have improved NM$ and other desirable traits as compared to the parent dam and as compared to other calves born in the herd.

The frozen inseminate obtained as provided below in Example 7 is also used for the generation of elite bulls and heifers. Frozen inseminate obtained as provided below in Example 7 is provided for artificial insemination to an elite DM animal having an NM$ index of at least 900. After gestation, the calf is genotyped and identified for predicted characteristics, composite traits, and predicted transmitting abilities. A calf having improved traits is selected and used for further breeding and for the improvement of existing herds.

Example 6: Characterization of LOCI

The sequence listing provides the results of the genotyping. Each sequence represents the sequence of a single SNP and the adjacent 100 base pairs (bp) of sequence on either side of the SNP. The sequences are listed first by homozygous alleles then heterozygous alleles and sorted by chromosome. Thus, SEQ ID NO:1 is the genotype of Animal at a first allele. Genomic sequences matching SEQ ID NO:1 are identified by BLAST search of the Bovine Genome Database (available online at bovinegenome(dot)org/bgd-_blast/) using any of the five available nucleotide datasets, but most conveniently using the Bos taurus UMD3.1 chromosome assembly with an e-value cuttoff of $10\times10^{-10}$. Blast identifies sequence GK000007.2, chromosome 7 having significant alignment (e.g., e-value of $1.42\times10^{-98}$ and total score of 363.76). Notably, as all the sequences in the sequence listing comprise sequences of 201 bp, the e-value and score for each sequence searched will be the same and dependent on the size of the sequence database. The sequence match identifies base number 41741927 as the start of the matching sequence and base 41742127 as the last matching base in a region of 100% identity without gaps. From the BLAST results, the matching sequence can be viewed in the genome browser, JBrowse, which allows for an extensive set of details to displayed, including polymorphisms from the Bovine HapMap SNP50 and the dbSNP databases. Analysis identifies the allelic locus at base position 101 (the SNP) corresponding to HapMap allelic locus ARS-BFGL-NGS-69727 and dbSNP allelic locus rs109034414. Analysis shows that SEQ ID NO:1 comprises the 'G' allele at this site. Thus, Animal is homozygous 'G' at the rs109034414/ARS-BFGL-NGS-69727 SNP locus ("the rs109034414 locus").

The BGD provides extensive information about the rs109034414 locus through "BovineMine," an integrated data warehouse for the BGD. From BovineMine, using either SNP identifier, though more conveniently the dbSNP identifier, information about the variation including aliases and importantly, identification of "Overlapping Features" such as linked genes and traits.

TABLE 11

Overlapping features of SEQ ID NO: 1

| Overlapping Features DB identifier | Feature | Abbreviation | Peak Centimorgan | Inheritance Model |
|---|---|---|---|---|
| 106490 | QTL: Calving ease (maternal) | CALEASE | 50.24 | Mendelian |
| 119779 | QTL: Heifer pregnancy | HPG | 50.19 | Mendelian |
| 31181 | QTL: Cold tolerance | COLDT | 61.47 | Mendelian |

As shown in Table 11, SEQ ID NO:1 is linked to three desirable QTL's, Calving ease, Heifer pregnancy and cold tolerance. Linkage of the sequences of Animal to desirable traits is not surprising given the multigenerational selection program that has led to the production of the elite germplasm. As a homozygous loci, it is more likely to transmit the desirable traits on to the progeny for improvements to existing herds. When bred with elite heifers, Animal's homozygous genes are likely to remain homozygous.

Example 7: Progeny Generation Using in vitro Fertilization and Embryo Transfer

Semen from mature Animal bulls is collected by electroejaculation or by other methods known in the art: The collected semen is frozen in straws per methods known in the art. Progeny are generated by thawing a straw of frozen semen and the thawed semen used for artificial insemination. In short, about 5 ml to about 15 ml of semen is collected from a bull after being electroejaculated and mixed with a suitable extender and cryoprotectant. About 10 ml of semen is collected and mixed with about 240 ml of Triladyl™ solution (Minitube of America in Verona, Wis). The mixture of semen, extender and cryoprotectant is then placed in plastic straws. Straws containing about 20 million motile sperm in a volume of about ½ ml are obtained and frozen until needed. Prior to use, frozen straws are thawed.

The collected semen of the present specification may be frozen according to standard methods in the art as discussed above.

Example 8: Generation of Multiple Embryos by Superovulation and In Vitro Fertilization The Animal inseminate collected as provided in Example 7 is used for in vitro fertilization of oocytes collected from a heifer or cow to create multiple embryos. The heifer or cow is treated with follicle stimulating hormone to induce multiple ovulations. Following superovulation, the donor heifer or cow is bred using artificial insemination of the Animal inseminate. About seven days after insemination, embryos are non-surgically collected by 'flushing' from the donor's uterus and transferred into synchronous recipients that serve as surrogate mothers. Embryos may be frozen for implantation at a later date.

Embryos are also generated using IVF collection of unfertilized oocytes from the ovaries of a donor cow or heifer. Oocytes are fertilized in vitro and transferred seven days after fertilization following incubation under controlled conditions. IVF collection and fertilization allows for the generation of multiple embryos obtained from open cows, pregnant cows, virgin heifers and females having difficulty in conventional breeding. IVF collection also provides for collection of oocytes from donors shortly after death.

Embryos are transferred to a surrogate and gestated until birth.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10982187B2). An electronic copy of the "Sequence Listing" will also be available from the USPTO upon request and payment of the fee set forth in 37 CFR 1.19(b)(3).

The invention claimed is:

1. A plurality of Bos taurus cells comprising HO840003150607238 germplasm, wherein a representative sample of HO840003150607238 germplasm has been deposited under ATCC Accession No. PTA-125702.

2. A frozen vial, a cell culture, a tissue, a zygote, or an embryo comprising the plurality of Bos taurus cells according to claim 1.

3. A plurality of Bos taurus gamete cells comprising HO840003150607238 germplasm, wherein a representative sample of HO840003150607238 germplasm has been deposited under ATCC Accession No. PTA-125702.

4. Fresh semen comprising the plurality of Bos taurus gamete cells according to claim 3, wherein said gamete cells are sperm cells.

5. A cryopreserved bovine inseminate comprising the plurality of Bos taurus gamete cells according to claim 3.

6. An F1 Bos taurus animal, or part thereof, wherein said F1 Bos taurus animal is an F1 progeny animal of a Bos taurus animal comprising HO840003150607238 germplasm, wherein a representative sample of HO840003150607238 germplasm has been deposited under ATCC Accession No. PTA-125702.

7. The F1 Bos taurus animal, or part thereof, according to claim 6, wherein said F1 Bos taurus animal is prepared by artificial conception.

8. The F1 Bos taurus animal, or part thereof, according to claim 7, wherein said artificial conception is in vitro fertilization and implantation, Artificial Insemination (AI), or in vivo insemination and embryo transfer (ET).

9. The F1 Bos taurus animal, or part thereof, according to claim 6, wherein said part thereof is an isolated oocyte or a plurality of sperm.

10. An inseminate composition comprising cryoprotectant and semen comprising Bos taurus HO840003150607238 gamete cells according to claim 3, wherein the gamete cells are sperm cells.

11. The F1 Bos taurus animal, or part thereof, according to claim 6, said part comprising an F1 Bos taurus inseminate comprising at least half of a haploid genome of Bos taurus HO840003150607238 germplasm.

12. A bull comprising the plurality of Bos taurus cells according to claim 1.

13. The plurality of Bos taurus gamete cells according to claim 3, wherein the gamete cells are sperm cells.

14. Semen comprising the plurality of Bos taurus sperm cells according to claim 13.

15. Semen according to claim 14, wherein the semen is an inseminate.

16. Semen according to claim 15, wherein said inseminate is contained in a straw.

17. Semen comprising the plurality of sperm according to claim 9.

18. Semen according to claim 17, wherein the semen is an inseminate.

19. Semen according to claim 18, wherein said inseminate is contained in a straw.

20. Semen according to claim 19, wherein the inseminate is cryopreserved.

21. The F1 Bos taurus animal, or part thereof, according to claim 6, comprising a gene edited genome.

22. The F1 Bos taurus animal, or part thereof, according to claim 21, wherein said gene edited genome is the gene edited genome of Bos taurus inseminate comprising at least half of a haploid genome of Bos taurus HO840003150607238 germplasm.

\* \* \* \* \*

Disclaimer

10,982,187 B2 - Devan Charles Funk, DeForest, WI (US); Katrina Dattilo, WI (US). BOS TAURUS VARIETY 'HO840000315067238' AND METHODS OF USE THEREOF. Patent dated April 20, 2021. Disclaimer filed May 26, 2022, by the assignee, ABS Global, Inc.

I hereby disclaim the following complete claims 1-22 of said patent.

*(Official Gazette, October 25, 2022)*